US010234464B2

(12) United States Patent
Block et al.

(10) Patent No.: US 10,234,464 B2
(45) Date of Patent: Mar. 19, 2019

(54) MARKER FOR STATIN TREATMENT STRATIFICATION IN HEART FAILURE

(71) Applicant: Roche Diagnostics Operations, Inc., Indianapolis, IN (US)

(72) Inventors: Dirk Block, Bichl (DE); Hans-Peter Brunner, Muenchenstein (CH); Thomas Dieterle, Freiburg (DE); Ursula-Henrike Wienhues-Thelen, Krailling (DE); Christian Zaugg, Rheinfelden (DE); Andre Ziegler, Laeufelfingen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/054,255

(22) Filed: Feb. 26, 2016

(65) Prior Publication Data
US 2016/0169911 A1 Jun. 16, 2016

Related U.S. Application Data

(63) Continuation of application No. PCT/EP2014/068090, filed on Aug. 26, 2014.

(30) Foreign Application Priority Data

Aug. 26, 2013 (EP) .................................... 13181687

(51) Int. Cl.
*G01N 33/50* (2006.01)
*G01N 33/68* (2006.01)
*A61K 31/40* (2006.01)
*G01N 33/62* (2006.01)

(52) U.S. Cl.
CPC ......... *G01N 33/6893* (2013.01); *A61K 31/40* (2013.01); *G01N 33/62* (2013.01); *G01N 33/6869* (2013.01); *G01N 33/6872* (2013.01); *G01N 2333/47* (2013.01); *G01N 2333/475* (2013.01); *G01N 2333/495* (2013.01); *G01N 2333/5412* (2013.01); *G01N 2800/325* (2013.01); *G01N 2800/52* (2013.01)

(58) Field of Classification Search
CPC ............... G01N 33/6893; G01N 33/62; G01N 33/6869; G01N 33/6872; G01N 2333/47; G01N 2333/475; G01N 2333/495; G01N 2333/5412; G01N 2800/325; G01N 2800/52; A61K 31/40
See application file for complete search history.

(56) References Cited

U.S. PATENT DOCUMENTS

| | | |
|---|---|---|
| 2007/0218498 A1 | 9/2007 | Buechler et al. |
| 2009/0155827 A1 | 6/2009 | Zeiher et al. |
| 2010/0255520 A1* | 10/2010 | Kavsak ............... G01N 33/6869 435/20 |
| 2011/0065204 A1 | 3/2011 | Wollert et al. |
| 2012/0029003 A1 | 2/2012 | Muntendam |
| 2012/0157378 A1* | 6/2012 | Liu ....................... C12Q 1/6883 514/6.9 |
| 2012/0219943 A1* | 8/2012 | Ky ...................... G01N 33/6893 435/6.11 |
| 2012/0264138 A1 | 10/2012 | Hess et al. |

FOREIGN PATENT DOCUMENTS

| | | | |
|---|---|---|---|
| EP | 2367006 A1 | 9/2011 | |
| WO | 2004/046722 A2 | 6/2004 | |
| WO | 2005/113585 A2 | 12/2005 | |
| WO | 2007/026214 A1 | 3/2007 | |
| WO | 2007/106811 A2 | 9/2007 | |
| WO | WO-2008089994 A1 * | 7/2008 | ......... G01N 33/6893 |
| WO | 2009/040133 A1 | 4/2009 | |
| WO | 2009/047283 A2 | 4/2009 | |
| WO | 2009/138451 A1 | 11/2009 | |
| WO | 2010/049538 A1 | 5/2010 | |
| WO | 2012/003475 A1 | 1/2012 | |

OTHER PUBLICATIONS

Zhang et al., Effects of Statin Therapy on Inflammatory Markers in Chronic Heart Failure: A Meta-analysis of Randomized Controlled Trials, Archives of Medical Research, 41, 2010, pp. 464-471.*
Abdelsalam et al., Correlation between urea level and HbA1c level in type 2 diabetic patients, Sudan Medical Laboratory Journal, 2011; 1(2), pp. 1-6.*
Soaly et al., Statin therapy in heart failure, Expert Rev. Cardiovasc. Ther. 3(1), 2005, pp. 5-7 (Year: 2005).*
Almansob, Mohammed Ahmed Saad et al., Simvastatin Reduces Myocardial Injury Undergoing Noncoronary Artery Cardiac Surgery A Randomized Controlled Trial, Arteriosclerosis, Thrombosis, and Vascular Biology, 2012, pp. 2304-2313, vol. 32.
Anand, Inder S. et al., Serial Measurement of Growth-Differentiation Factor-15 in Heart Failure Relation to Disease Severity and Prognosis in the Valsartan Heart Failure Trial, Circulation, 2010, pp. 1387-1395, vol. 122.

(Continued)

*Primary Examiner* — Gary Counts
(74) *Attorney, Agent, or Firm* — Roche Diagnostics Operations, Inc.

(57) ABSTRACT

The present invention is directed to a method of identifying a patient having heart failure as likely to respond to a therapy comprising a statin. The method is based on measuring the level of at least one marker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from a patient. Further envisaged is a method of predicting the risk of a patient to suffer from death or hospitalization, wherein said patient has heart failure and undergoes a therapy comprising a statin. The method is also based on the measurement of the level of at least one of the aforementioned markers.

10 Claims, 29 Drawing Sheets

(56) References Cited

OTHER PUBLICATIONS

Bui, An H. et al., Elevated concentration of placental growth factor (PlGF) and long term risk in patients with acute coronary syndrome in the PROVE IT-TIMI 22 trial, Journal of Thrombosis and Thrombolysis, 2012, pp. 222-228, vol. 34.
Cauthen, Clay et al., Relation of Blood Urea Nitrogen to Long-Term Mortality in Patients With Heart Failure, The American Journal of Cardiology, 2008, pp. 1643-1647, vol. 101.
Deswal, Anita et al., Cytokines and Cytokine Receptors in Advanced Heart Failure an Analysis of the Cytokine Database from the Vesnarinone Trial (VEST), Circulation, 2001, pp. 2055-2059, vol. 103.
Filippatos, Gerasimos et al., Prognostic Value of Blood Urea Nitrogen in Patients Hospitalized With Worsening Heart Failure: Insights From the Acute and Chronic Therapeutic Impact of a Vasopressin Antagonist in Chronic Heart Failure (ACTIV in CHF) Study, Journal of Cardiac Failure, 2007, pp. 360-364, vol. 13, No. 5.
Hall, Susan A. et al., Do Statins Affect Androgen Levels in Men? Results from the Boston Area Community Health Survey, Cancer Epidemiology, Biomarkers & Prevention, 2007, pp. 1587-1594, vol. 16, No. 8.
International Search Report dated Mar. 19, 2015, in Application No. PCT/EP2014/068090, 9 pages.
Kempf, Tibor et al., Prognostic Utility of Growth Differentiation Factor-15 in Patients With Chronic Heart Failure, Journal of the American College of Cardiology, 2007, pp. 1054-1060, vol. 50, No. 11.
Lenderink, Timo et al., Elevated Placental Growth Factor Levels Are Associated With Adverse Outcomes at Four-Year Follow-Up in Patients With Acute Coronary Syndromes, Journal of the American College of Cardiology, 2006, pp. 307-311, vol. 47, No. 2.
Nakamura, Tomohiro et al., Elevation of plasma placental growth factor in the patients with ischemic cardiomyopathy, International Journal of Cardiology, 2009, pp. 186-191, vol. 131.
Node, Koichi et al., Short-Term Statin Therapy Improves Cardiac Function and Symptoms in Patients With Idiopathic Dilated Cardiomyopathy, Circulation, 2003, pp. 839-843, vol. 108.
Pascual-Figal, Domingo A. et al., Sex Hormone-Binding Globulin: A New Marker of Disease Severity and Prognosis in Men With Chronic Heart Failure, Revista Española de Cardiologia, 2009, pp. 1381-1387, vol. 62, No. 12.
Seta, Yukihiro et al., Basic Mechanisms in Heart Failure: The Cytokine Hypothesis, Journal of Cardiac Failure, 1996, pp. 243-249, vol. 2, No. 3.
Sola, Srikanth et al., Atorvastatin Improves Left Ventricular Systolic Function and Serum Markers of Inflammation in Nonischemic Heart Failure, Journal of the American College of Cardiology, 2006, pp. 332-337, vol. 47, No. 2.
Stanworth, Roger D. et al., Statin Therapy Is Associated With Lower Total but Not Bioavailable or Free Testosterone in Men With Type 2 Diabetes, Diabetes Care, 2009, pp. 541-546, vol. 32, No. 4.
Wollert, Kai C. et al., Growth Differentiation Factor 15 for Risk Stratification and Selection of an Invasive Treatment Strategy in Non-ST-Elevation Acute Coronary Syndrome, Circulation, 2007, pp. 1540-1548, vol. 116.
Bauskin, Asne R. et al., The propeptide of macrophage inhibitory cytokine (MIC-1), a TGF-β superfamily member, acts as a quality control determinant for correctly folded MIC-1, The EMBO Journal, 2000, pp. 2212-2220, vol. 19, No. 10.
Bonaca, Marc P. et al., Growth Differentiation Factor-15 and Risk of Recurrent Events in Patients Stabilized After Acute Coronary Syndrome Observations from PROVE IT-TIMI 22, Arteriosclerosis and Thrombosis: A Journal of Vascular Biology, 2011, pp. 203-210, vol. 31.
Cleland, John G. F. et al., Plasma Concentration of Amino-Terminal Pro-Brain Natriuretic Peptide in Chronic Heart Failure: Prediction of Cardiovascular Events and Interaction With the Effects of Rosuvastatin, Journal of the American College of Cardiology, 2009, pp. 1850-1859, vol. 54, No. 20.
Denhardt, David T. and Guo, Xiaojia, Osteopontin: a protein with diverse functions, FASEB Journal, 1993, pp. 1475-1482, vol. 7.
Dickstein, Kenneth et al., Effects of losartan and captopril on mortality and morbidity in high-risk patients after acute myocardial infarction: the OPTIMAAL randomised trial, Lancet, 2002, pp. 752-760, vol. 360.
Gullestad, Lars et al., Galectin-3 predicts response to statin therapy in the Controlled Rosuvastatin Multinational Trial in Heart Failure (CORONA), European Heart Journal, 2012, pp. 2290-2296, vol. 33.
Hromas. Robert et al., PLAB, a novel placental bone morphogenetic protein, Biochimica et Biophysica Acta, 1997, pp. 40-44, vol. 1354.
Maglione, Domenico et al., Two alternative mRNAs coding for the angiogenic factor, placenta growth factor (PlGF), are transcribed from a single gene of chromosome 14, Oncogene, 1993, pp. 2333-2339, vol. 8.
Masson, Serge et al., An Update on Cardiac Troponins as Circulating Biomarkers in Heart Failure, Current Heart Failure Reports, 2010, pp. 15-21, vol. 7.
Sola, Srikanth et al., Statin Therapy Is Associated With Improved Cardiovascular Outcomes and Levels of Inflammatory Markers in Patients With Heart Failure, Journal of Cardiac Failure, 2005, pp. 607-612, vol. 11, No. 8.
Tavazzi, Luigi et al., Effect of rosuvastatin in patients with chronic heart failure (the GISSI-HF trial): a randomized, double-blind, placebo-controlled trial, Lancet, 2008, pp. 1231-1239, vol. 372.
Yokoyama-Kobayashi, Midori et al., Human cDNA Encoding a Novel TGF-β Superfamily Protein Highly Expressed in Placenta, Journal of Biochemistry, 1997, pp. 622-626, vol. 122, No. 3.
Gaggin, Hanna K. and Januzzi, James L., Jr., Biomarkers and diagnostics in heart failure, Biochimica et Biophysica Acta, 2013, pp. 2442-2450, vol. 1832.
Taimeh, Ziad et al., Vascular endothelial growth factor in heart failure, Nature Reviews Cardiology, 2013, pp. 519-530, vol. 10.
Wang, Yaling et al., The change and clinical significance of serum placenta growth factor in patients with chronic heart failure, Journal of Clinical Cardiology, 2009, pp. 251-253, vol. 25, No. 4, English portions only.
European Search Report dated Oct. 31, 2018, in Application No. EP 18185485.2, 2 pages.
Kodama, Yasushi et al., Atorvastatin Increases Plasma Soluble Fms-Like Tyrosine Kinase-1 and Decreases Vascular Endothelial Growth Factor and Placental Growth Factor in Association With Improvement of Ventricular Function in Acute Myocardial Infarction, Journal of the American College of Cardiology, 2006, pp. 43-50, vol. 48, No. 1.
Ky, Bonnie et al.., The Vascular Marker Soluble Fms-like Tyrosine Kinase 1 is Associated with Disease Severity and Adverse Outcomes in Chronic Heart Failure, Journal of the American College of Cardiology, 2011, pp. 386-394, vol. 58, No. 4.
Onoue, Kenji et al., Reduction of Circulating Soluble Fms-Like Tyrosine Kinase-1 Plays a Significant Role in Renal Dysfunction-Associated Aggravation of Atherosclerosis, Circulation, 2009, pp. 2470-2477, vol. 120.

\* cited by examiner

Data above median at baseline

Data below median at baseline

Data above median at baseline

Data below median at baseline

MARKER FOR STATIN TREATMENT STRATIFICATION IN HEART FAILURE

BACKGROUND OF THE DISCLOSURE

Heart failure (HF) is among the leading causes of morbidity and mortality in many countries worldwide. Apart from Ivabradine and Cardiac Resynchronization Therapy (CRT), there have been no novel therapies for heart failure in the past years. In contrast, most drug candidates of the last decade have failed in development phase III or before.

At the same time, statin therapy has become the cornerstone treatment in primary and secondary prevention of coronary artery disease (CAD). Although CAD underlies many cases of heart failure, the use of statin therapy in chronic heart failure (CHF) is not supported by major guidelines. This is because large phase III trials of statins in CHF have been neutral. Specifically, the CORONA and the GISSI-HF trials prospectively investigated the use of rosuvastatin 10 mg daily in patients with CHF (J Am Coll Cardiol 2009; 54: 1850-9; Lancet 2008; 372: 1231-9). Both trials failed to demonstrate a beneficial effect of statin treatment on their primary end point.

The results of the CORONA and the GISSI-HF trial led to the preclusion of statin treatment in HF guidelines. However, there may be a subgroup of HF patients that could derive a benefit from statin therapy. A post-hoc analysis of the Heart Protection Study (Lancet. 2002; 360: 7-22) and the CORONA trial revealed a decreased benefit of statin treatment in patients with higher NT-proBNP levels. Similarly, statins were less beneficial in patients with high Galectin-3 levels (Eur Heart J. 2012; 33:2290-6). However, this finding about Galectin-3 and statin benefits could not be substantiated in an analysis of the GISSI-HF study (Latini R., personal communication).

Bonaca et al. 2011 (Arterioscler Thromb Vasc Biol. 2011 January; 31(1):203-10) discloses a study in which it is analyzed whether GDF-15 at hospital discharge can be used as a marker for the assessment of the risk of death, recurrent myocardial infarction, and congestive heart failure. It is further analyzed whether these risks can be modified by statins. According to Bonaca, GDF-15 is not a suitable marker for therapeutic efficacy of statin treatment.

WO 09/047283 discloses a method of deciding which treatment or combination of treatments including statin treatment is to be applied in a remodeling process of a patient after a myocardial infarction which is based on the detection of three markers: natriuretic peptide, a cardiac troponin, and an inflammatory marker like GDF-15. The document, however, does not pertain to the stratification of treatment of a heart failure patient with a statin.

US 2011/0065204 discloses a method for identifying susceptibility of a patient to therapy for heart failure which is based on the quantification of GDF-15 in a sample from the patient suffering from heart failure. Statin treatment is mentioned as a possible treatment of the patients enrolled in the study described in the examples but not as a therapy for heart failure. Moreover, GDF-15 is not disclosed as a marker which can be used for identifying a patient as likely to respond to statin therapy or not.

WO 2009/138451 discloses a method of deciding which statin medication is to be applied in an apparently stable patient suffering from heart failure and undergoing a change in physiological state, the method comprising repeatedly determining, within a given time interval, an amount of the peptide markers NT-proANP, NT-proBNP, a cardiac troponin, and GDF-15 in a sample from the patient.

Sola et al. (J Card Fail. 2005 October; 11 (8):607-12) discloses that in heart failure patients treated with statins the IL-6-level decrease showing that statins exert a positive influence on inflammatory processes. The publication does not disclose that IL-6 can be used for the stratification before the therapeutic use of statins in heart failure patients.

WO 2007/26214 discloses a method of predicting patient response to a drug or drug candidate. As one of several drugs, statins are mentioned.

In the context of the studies underlying the present invention, it was advantageously shown that GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) can be used in order to identify subgroups of heart failure patients responding to statin therapy. In particular, biomarker levels in blood may predict whether a heart failure patient will derive a benefit or will derive harm from statin therapy.

BRIEF SUMMARY OF THE DISCLOSURE

The present invention is directed to a method of identifying a patient having heart failure as likely to respond to a therapy comprising a statin. The method is based on measuring the level of at least one marker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from a patient. Further envisaged is a method of predicting the risk of a patient to suffer from death or hospitalization, wherein said patient has heart failure and undergoes a therapy comprising a statin. The method is also based on the measurement of the level of at least one of the aforementioned markers.

DETAILED DESCRIPTION OF THE DISCLOSURE

Figure 1:
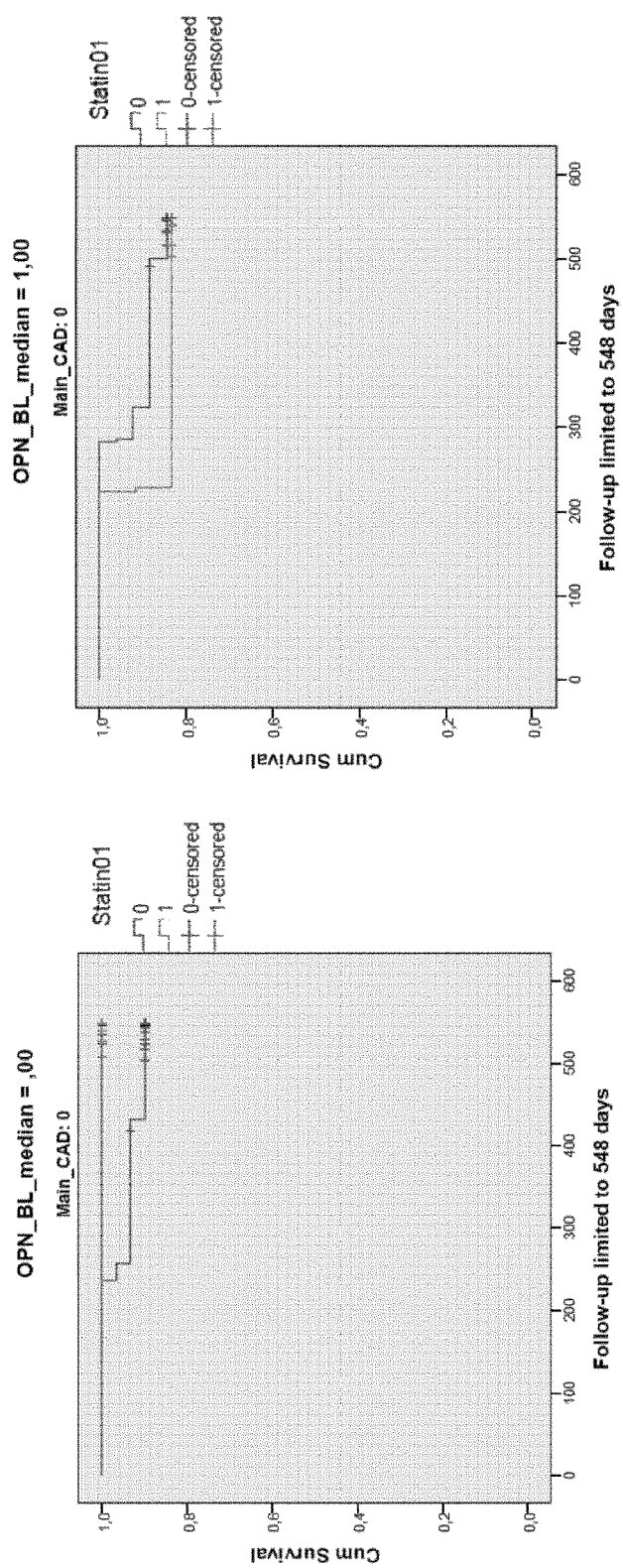
FIG. 1 Kaplan-Meier curves for time to first HF hospitalization or death split by CAD, statin therapy (0=no statin, n=211, 1=on statin therapy, n=288), and biomarker median levels at baseline (0=below median, 1=above median; occasionally 1=below median, 2=above median); CAD=0: patients w/o coronary artery disease, CAD=1 patients with coronary artery disease
Figure 1:
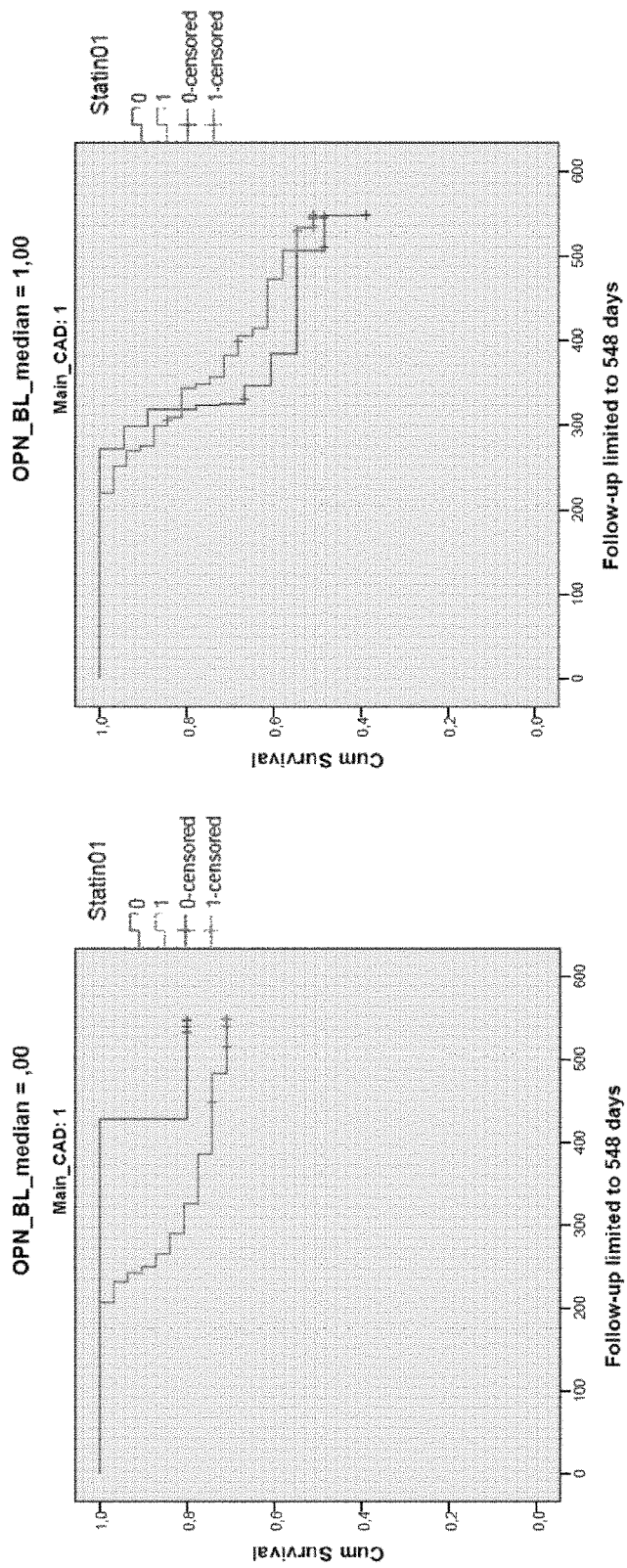
Figure 1:
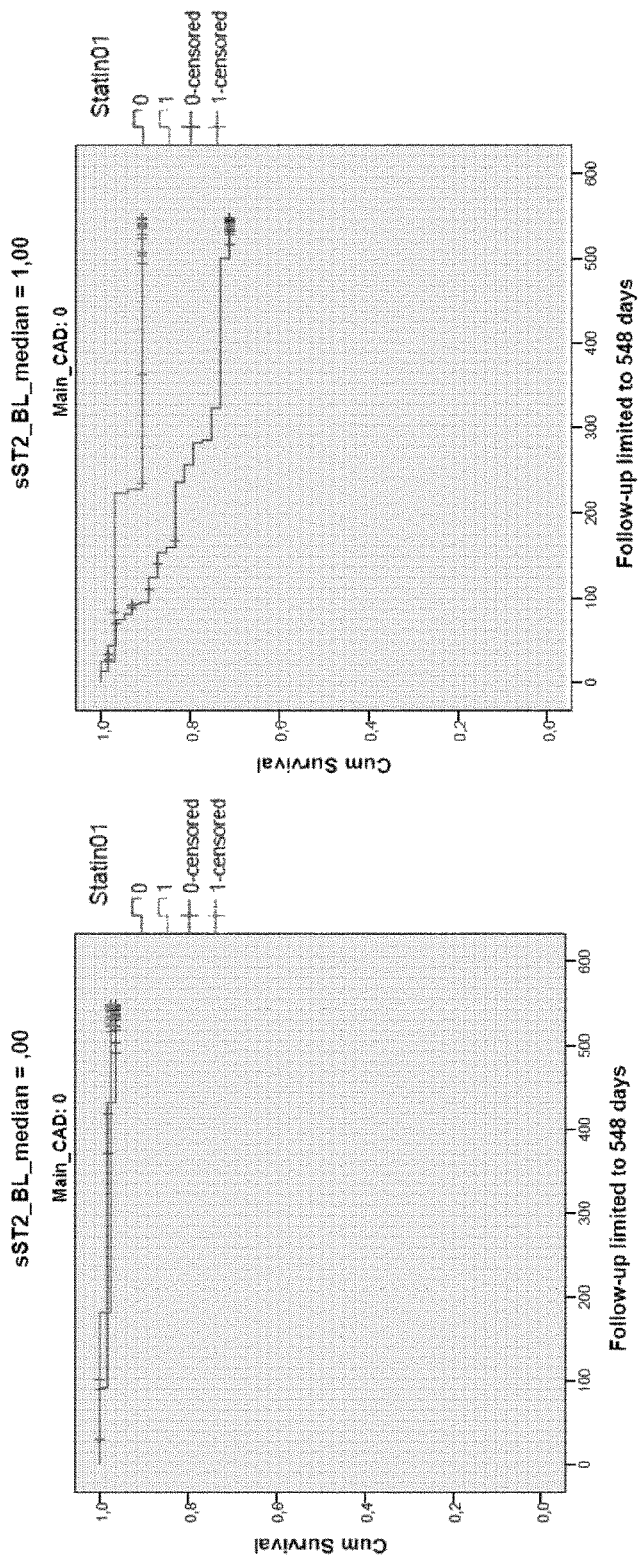
Figure 1:
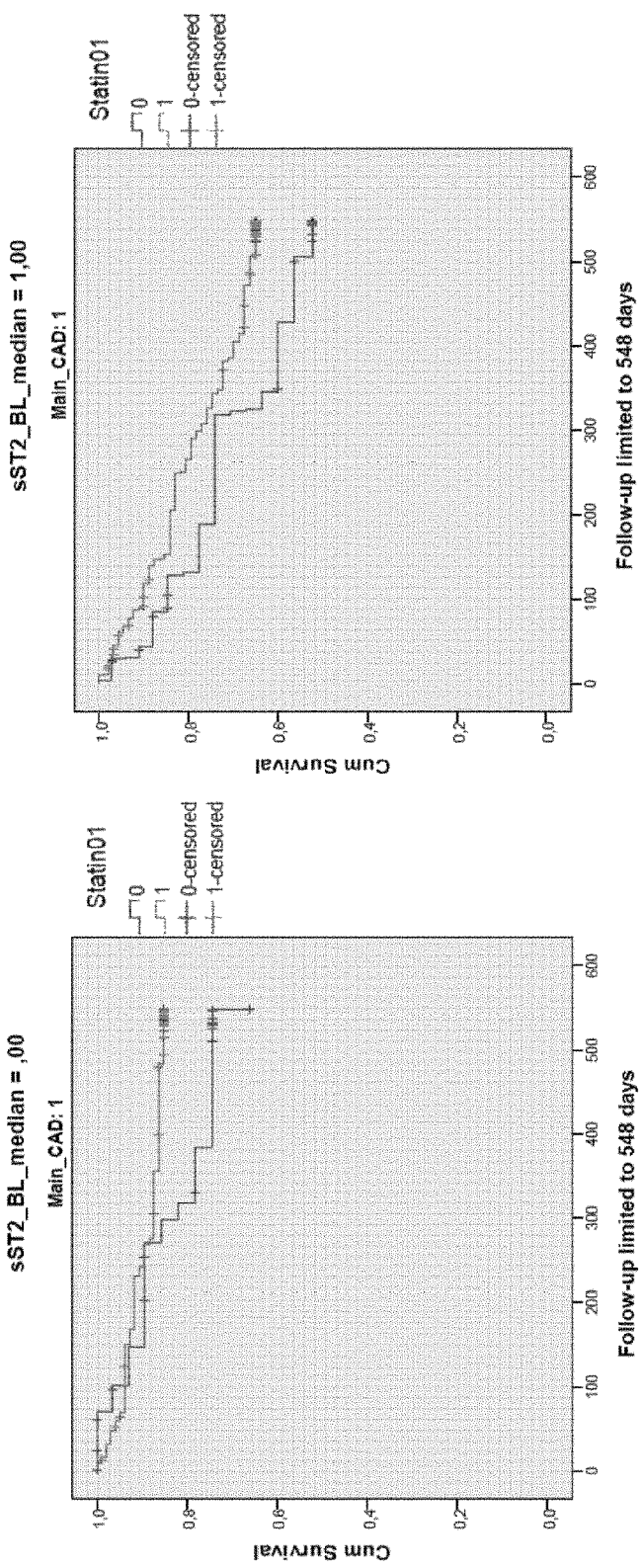
Figure 1:
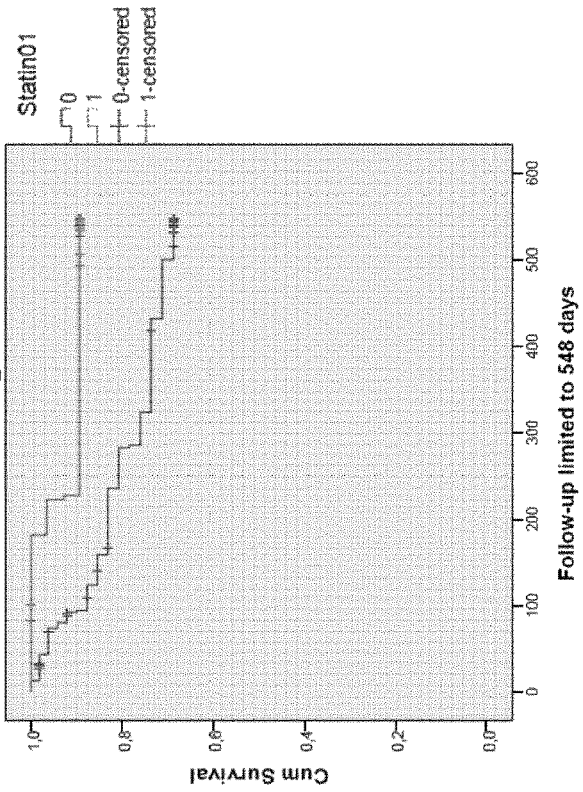
Figure 1:
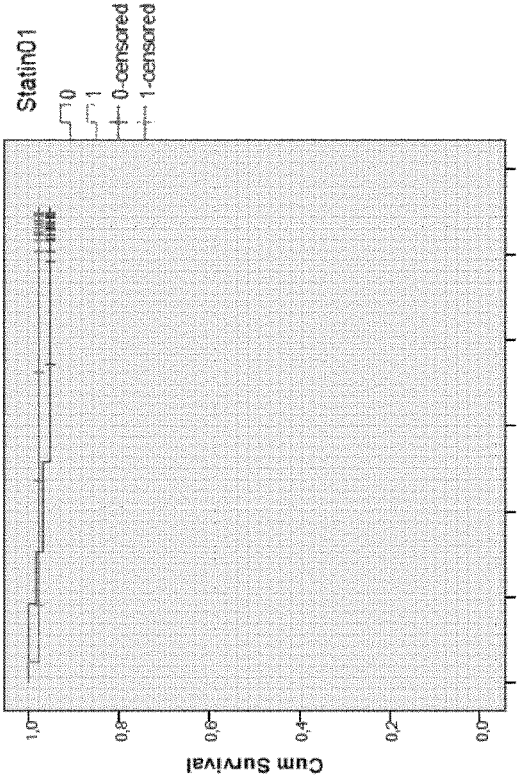
Figure 1:
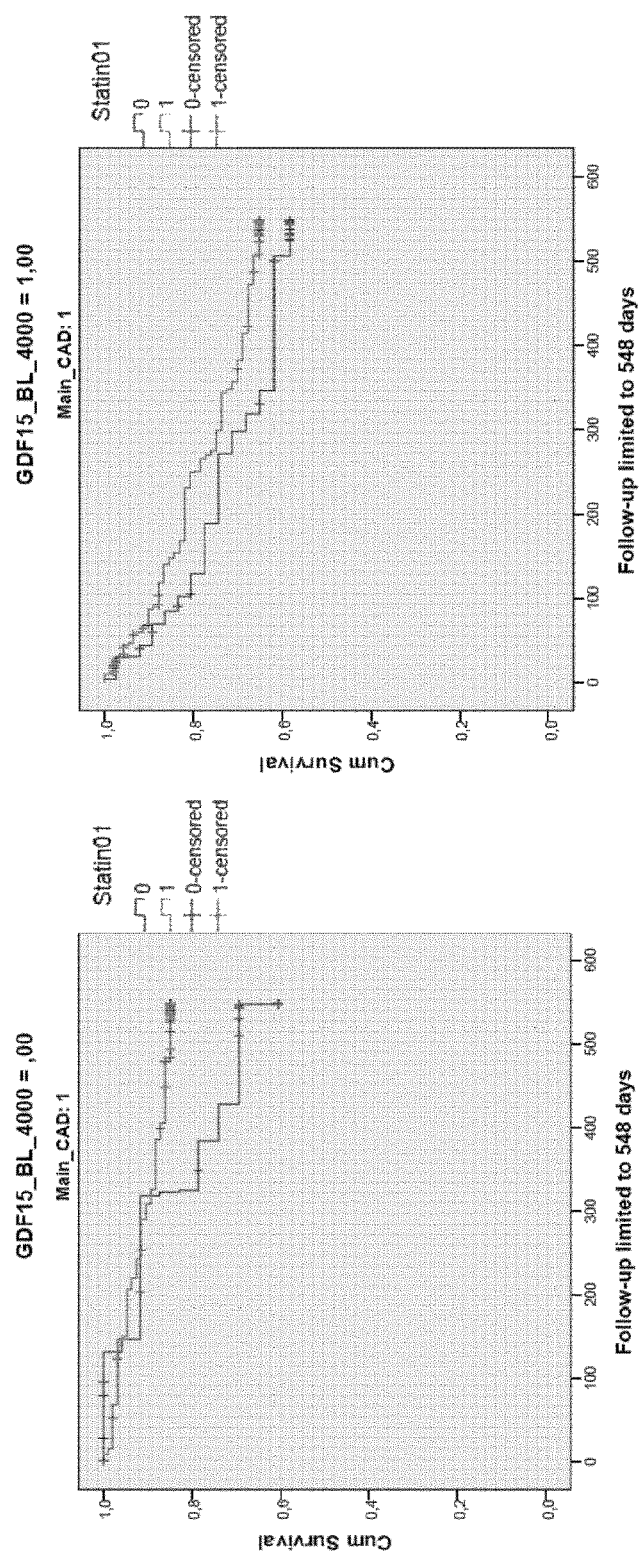
Figure 1:
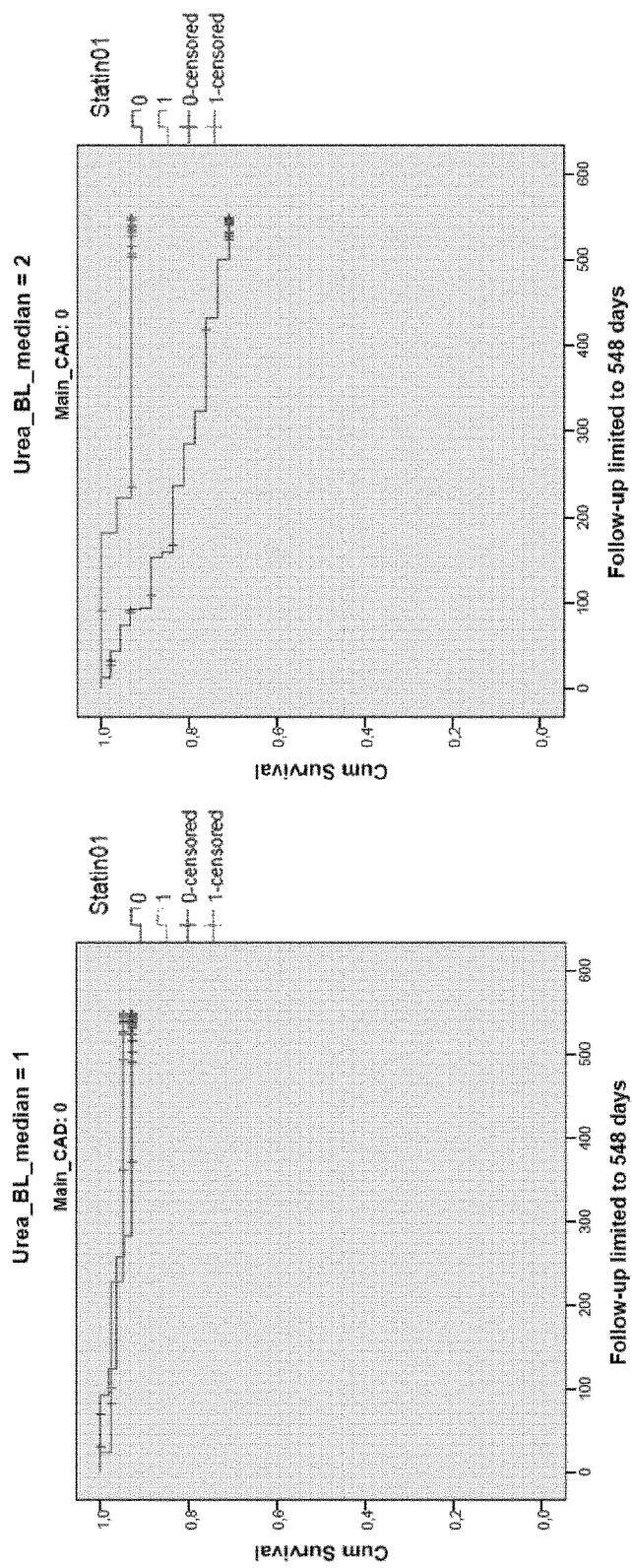
Figure 1:
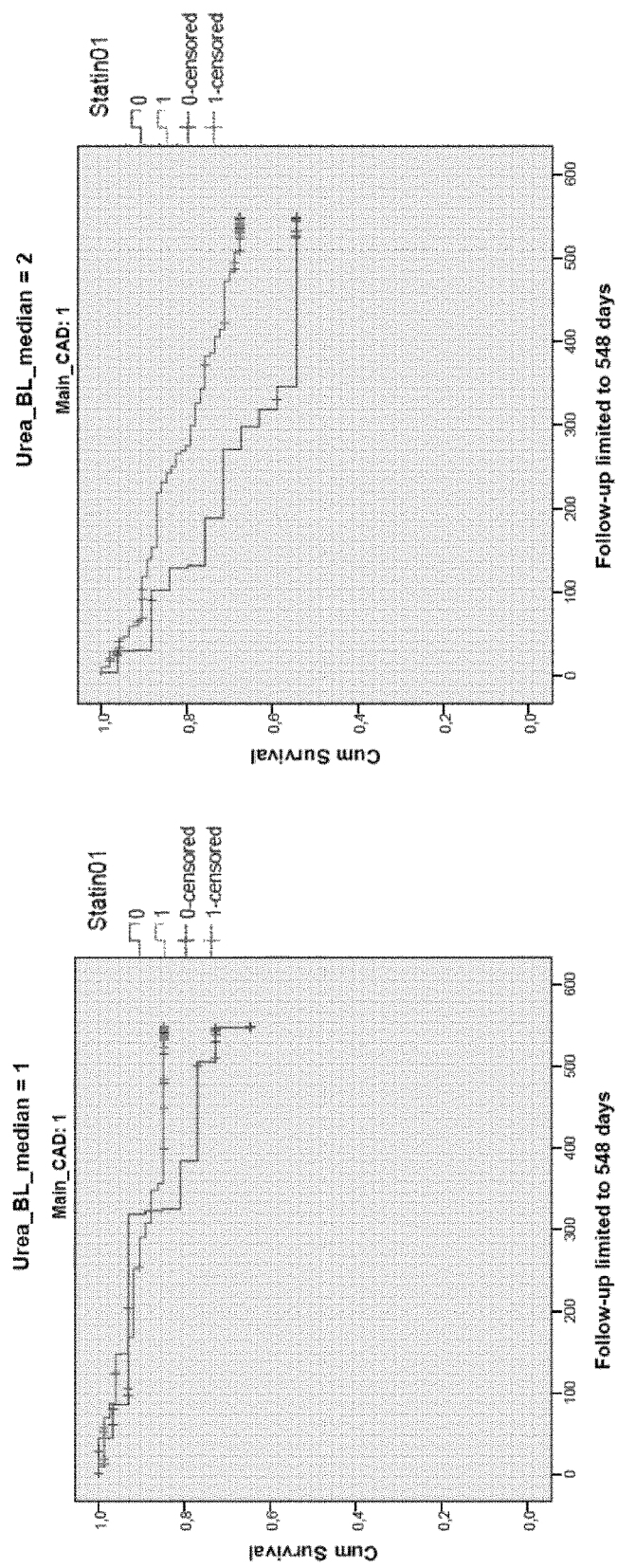
Figure 1:
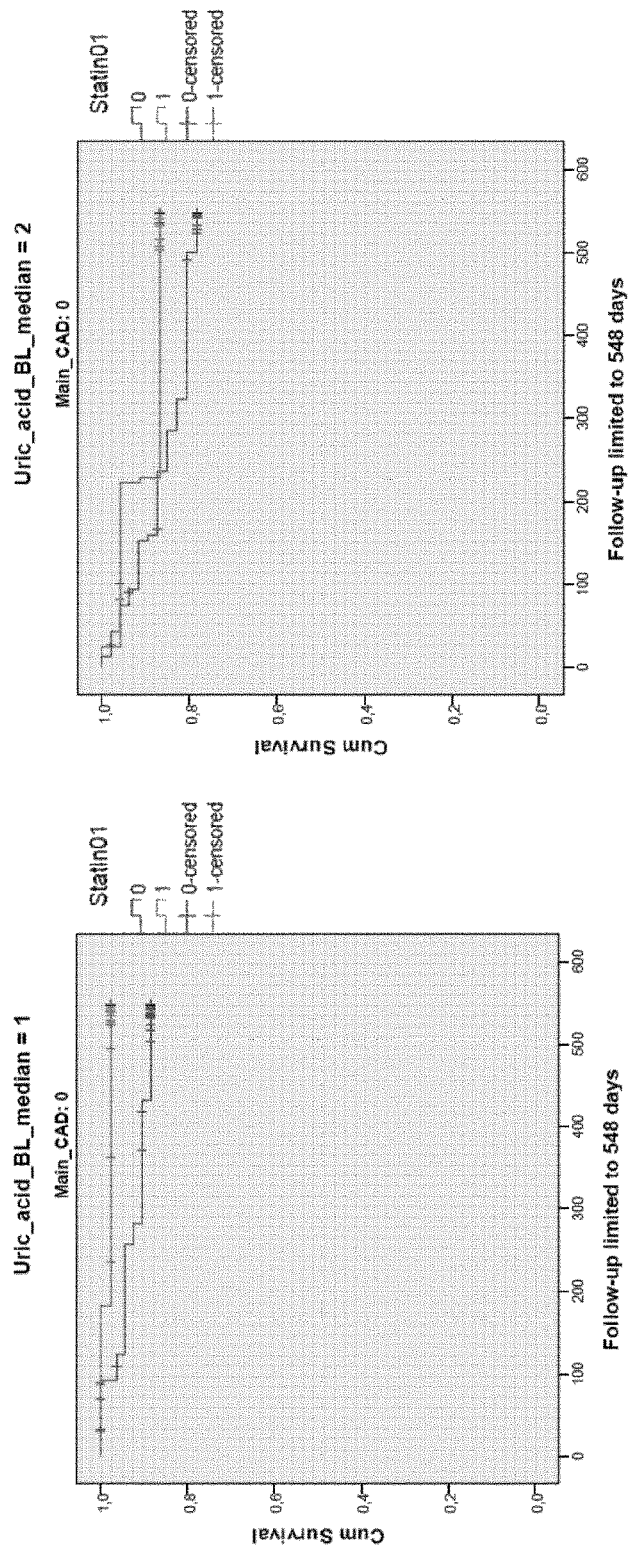
Figure 1:
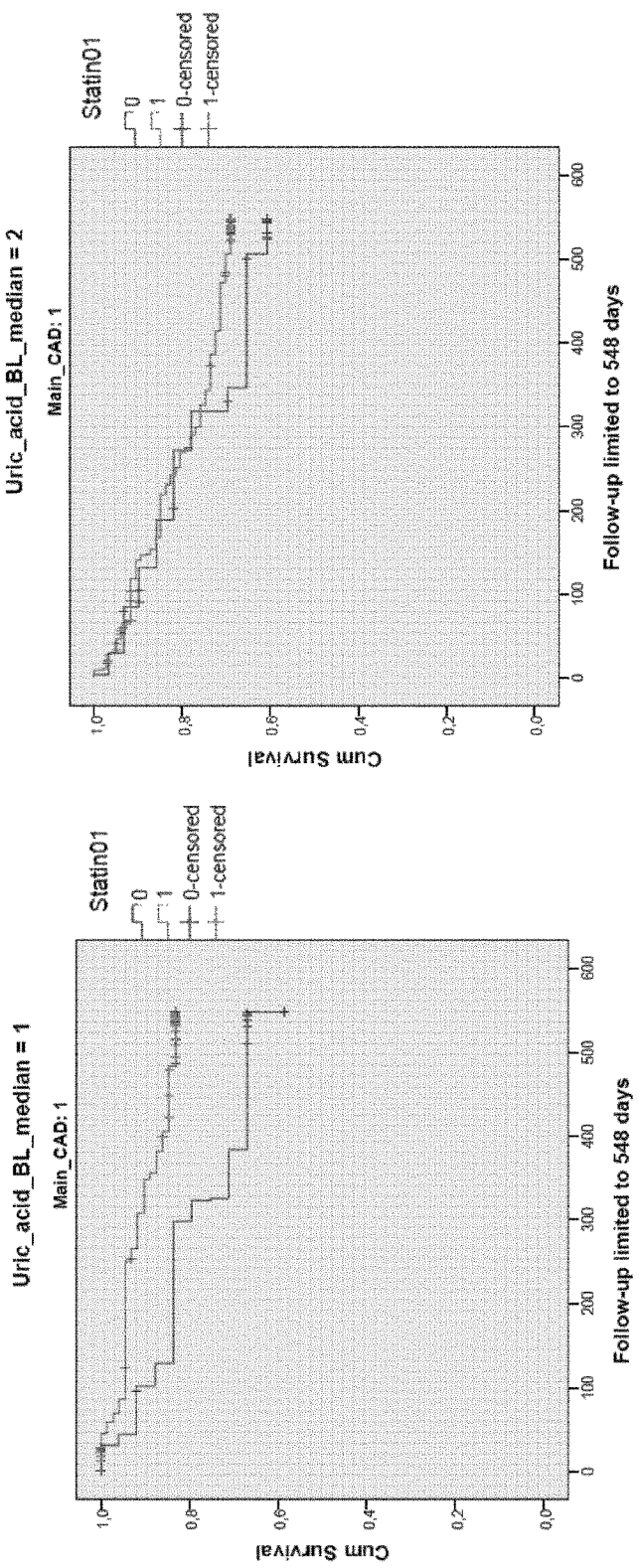
Figure 1:
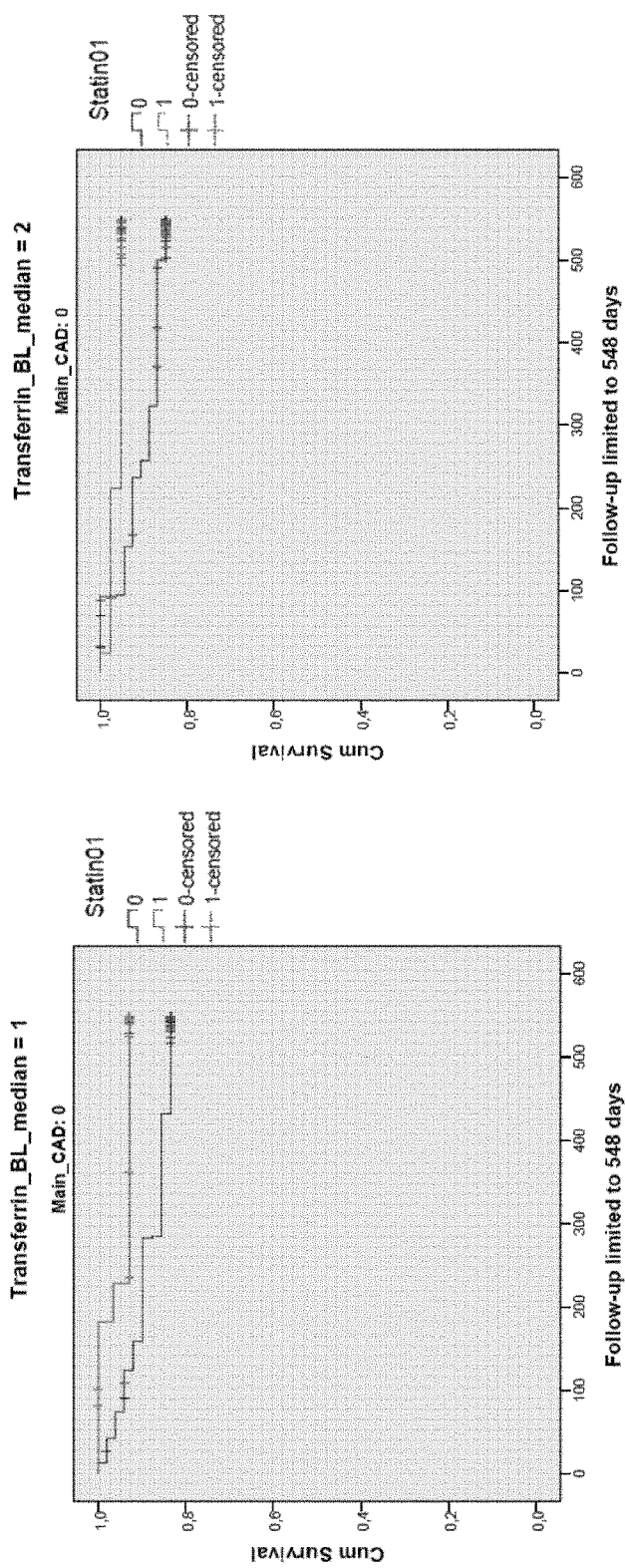
Figure 1:
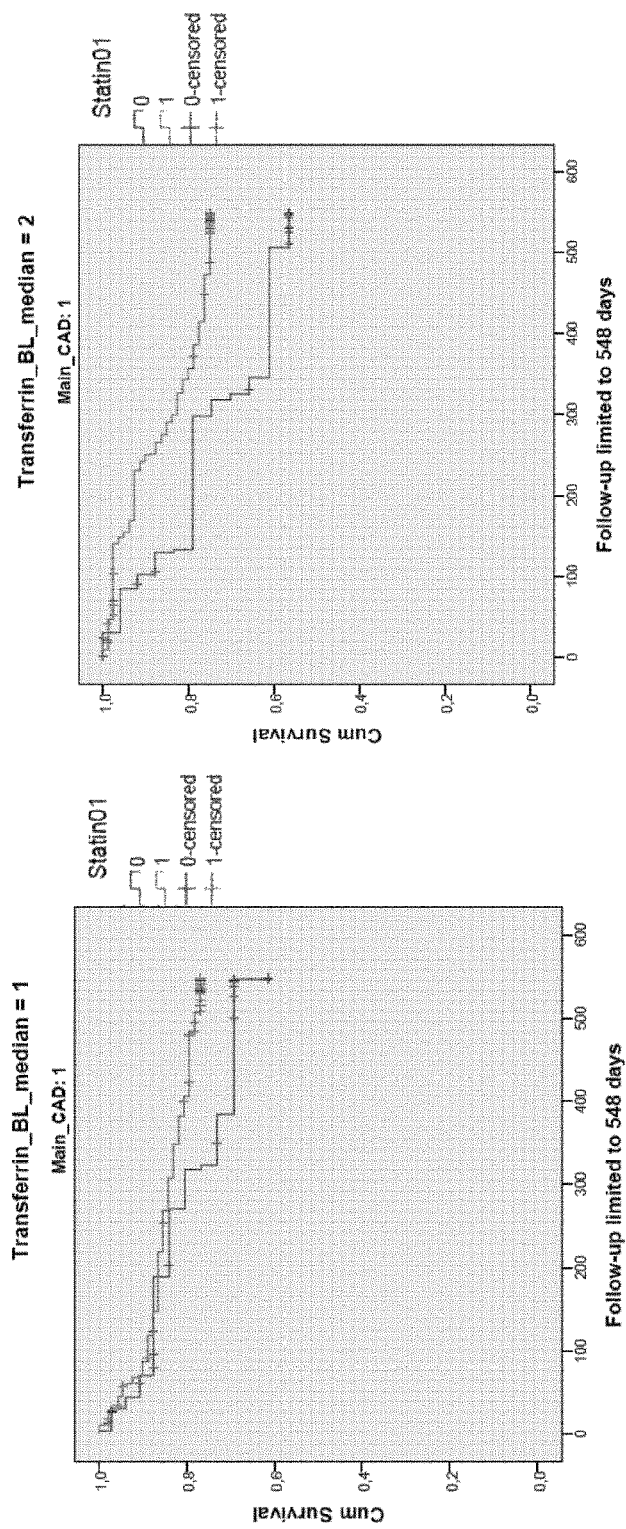
Figure 1:
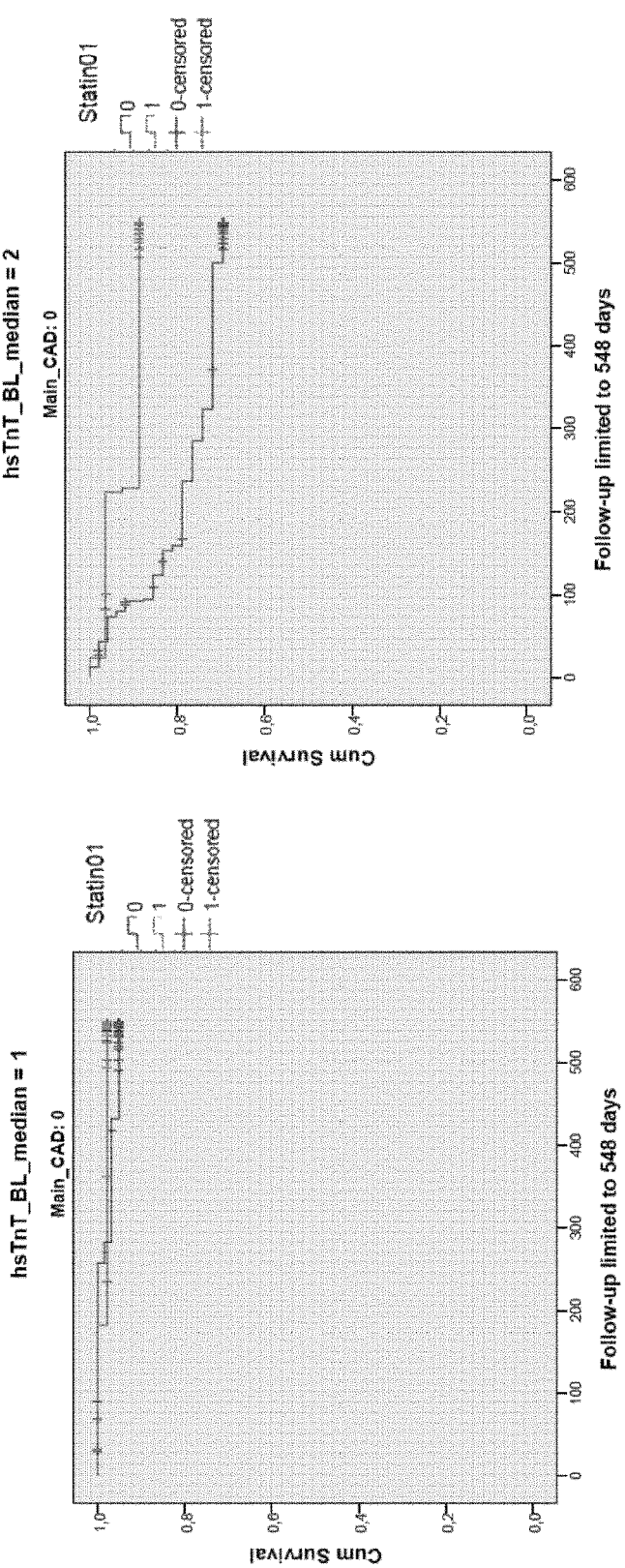
Figure 1:
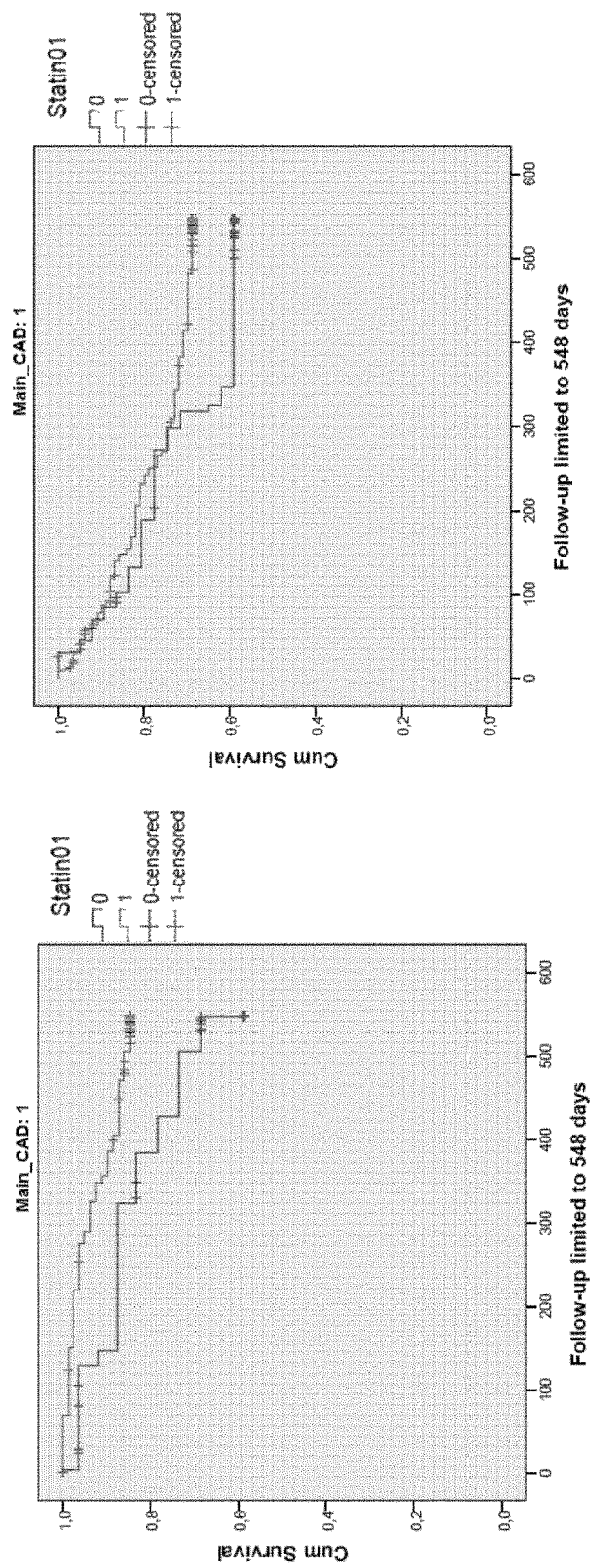
Figure 1:
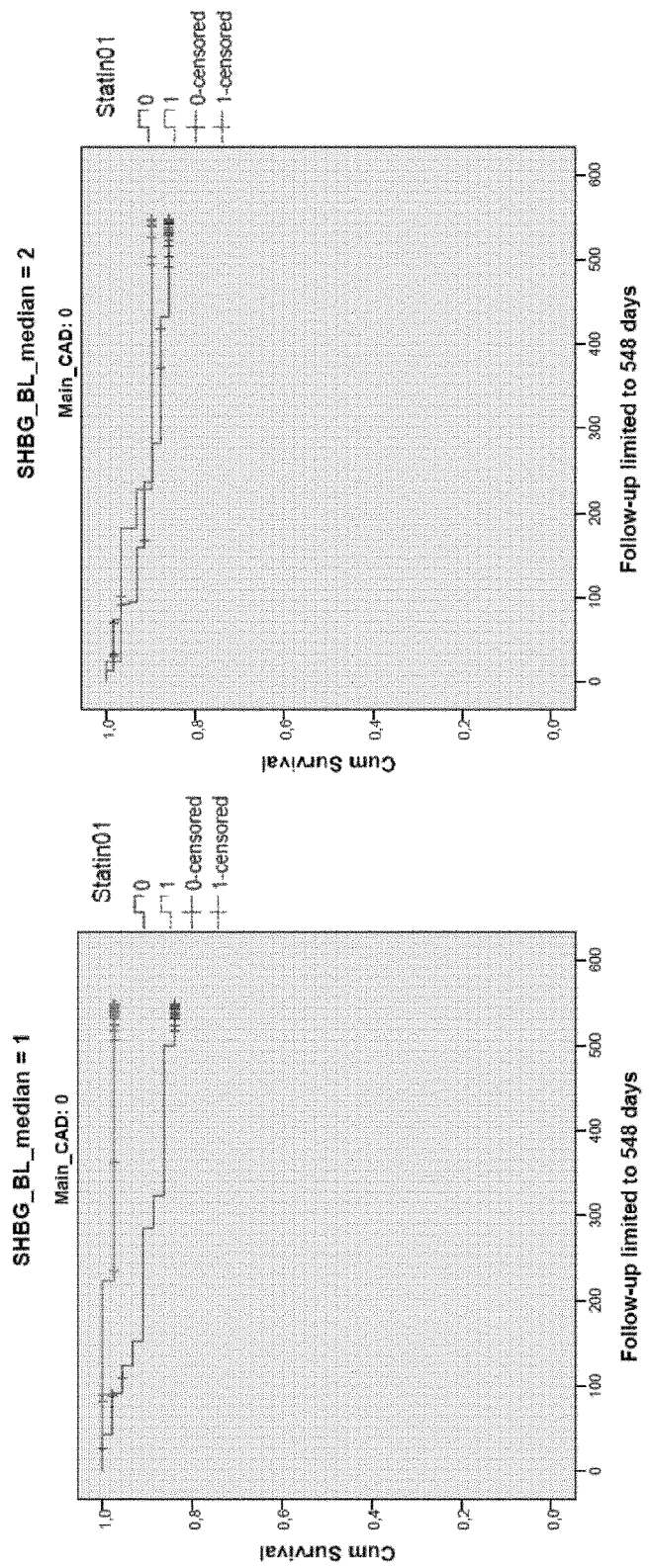
Figure 1:
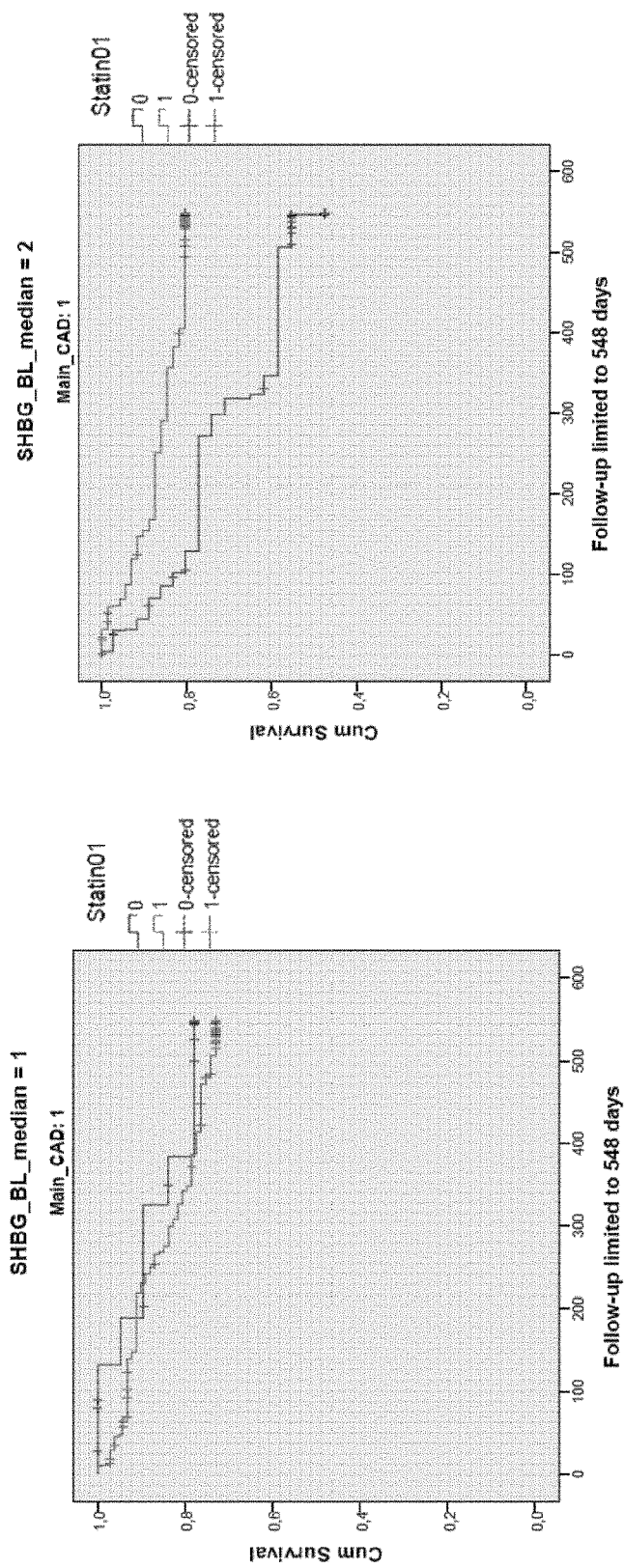
Figure 1:
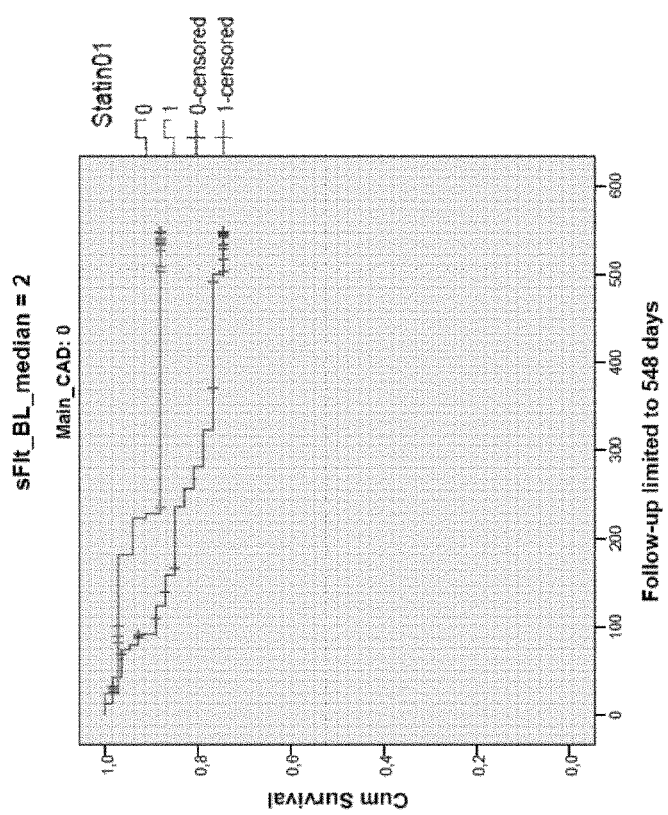
Figure 1:
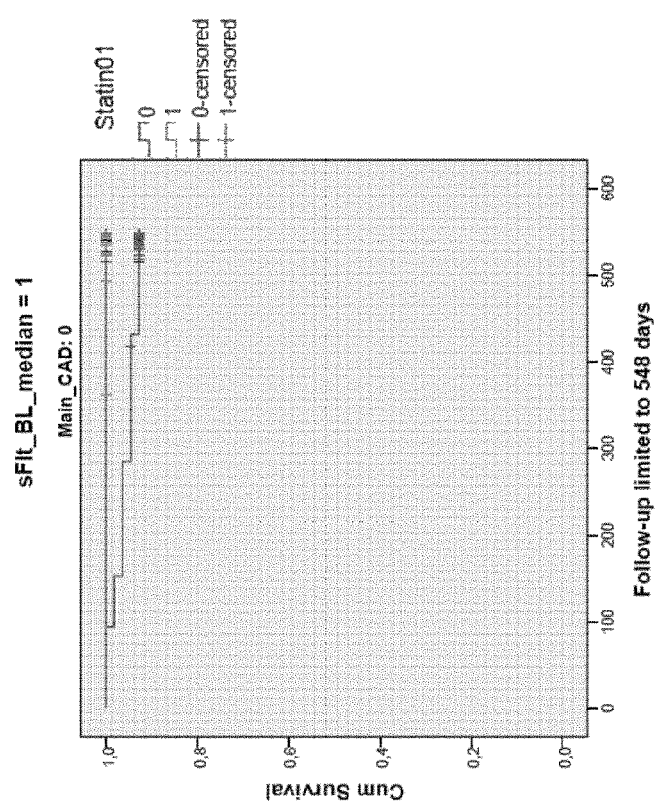
Figure 1:
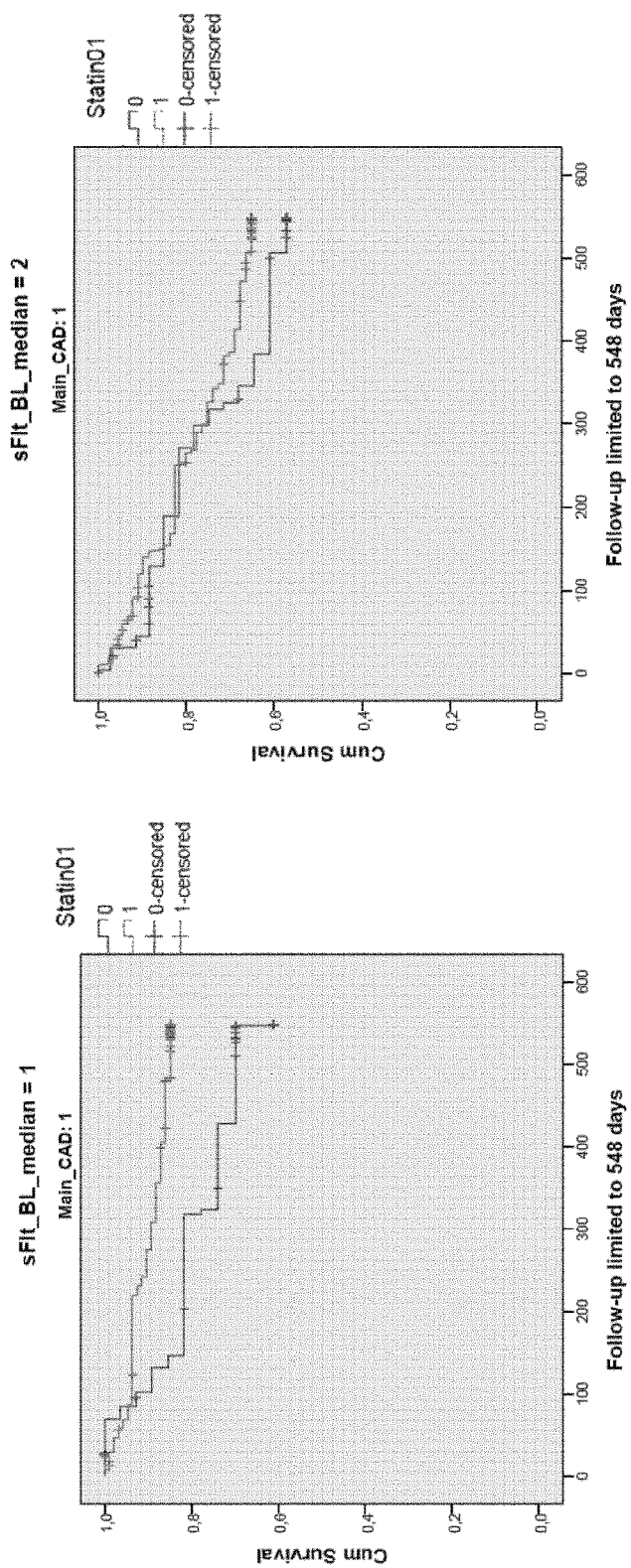
Figure 1:
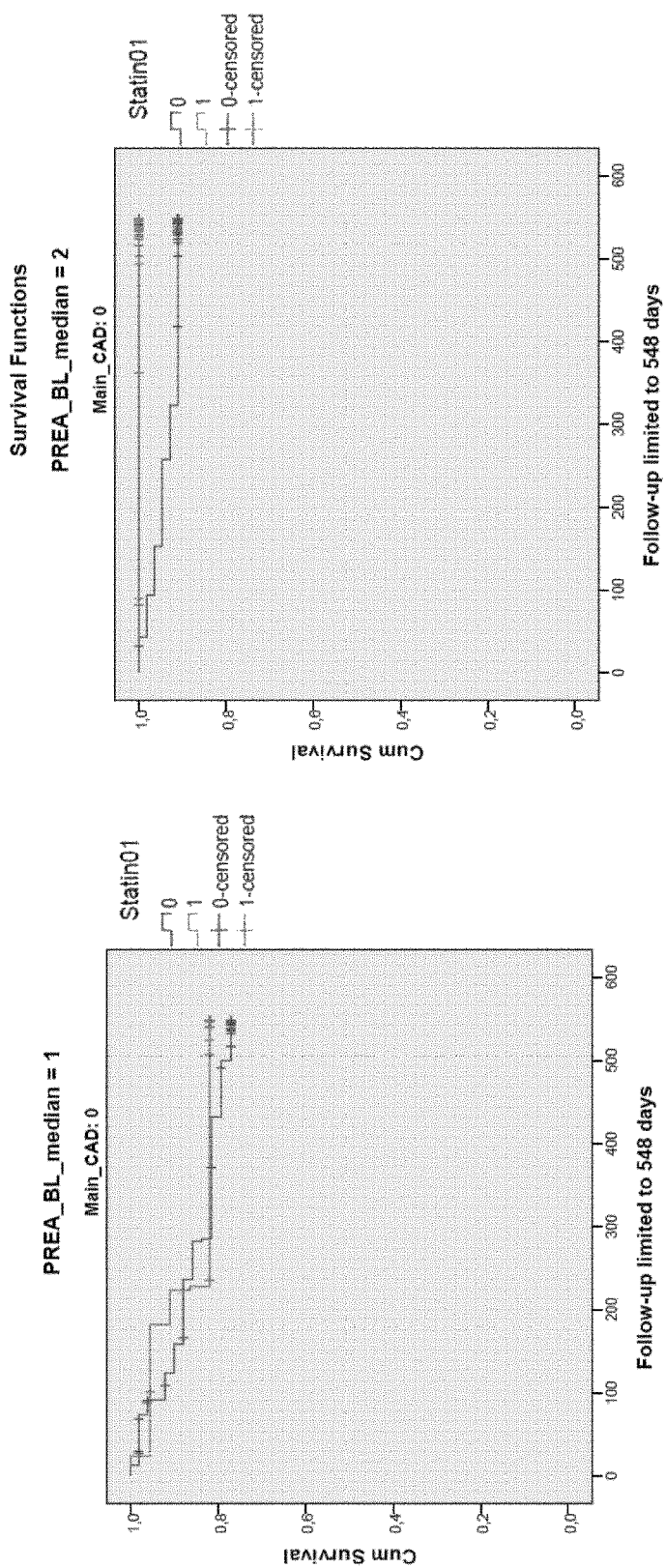
Figure 1:
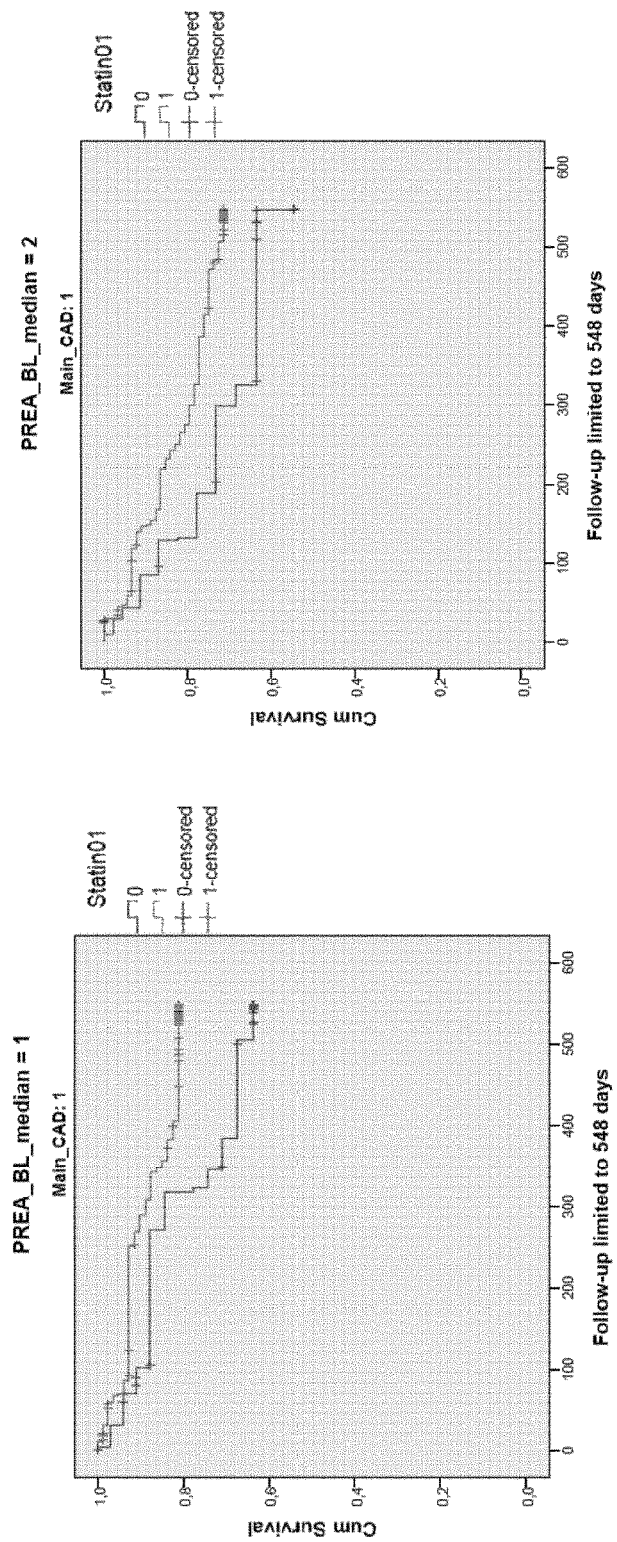
Figure 1:
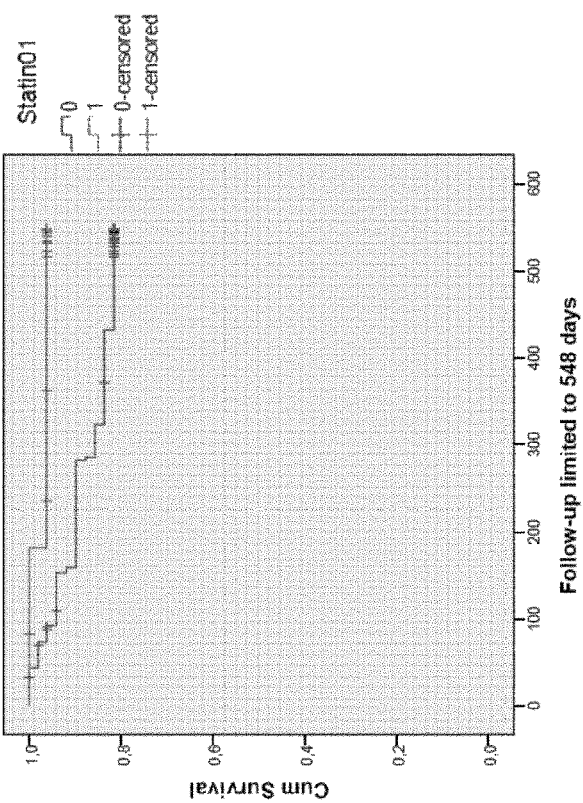
Figure 1:
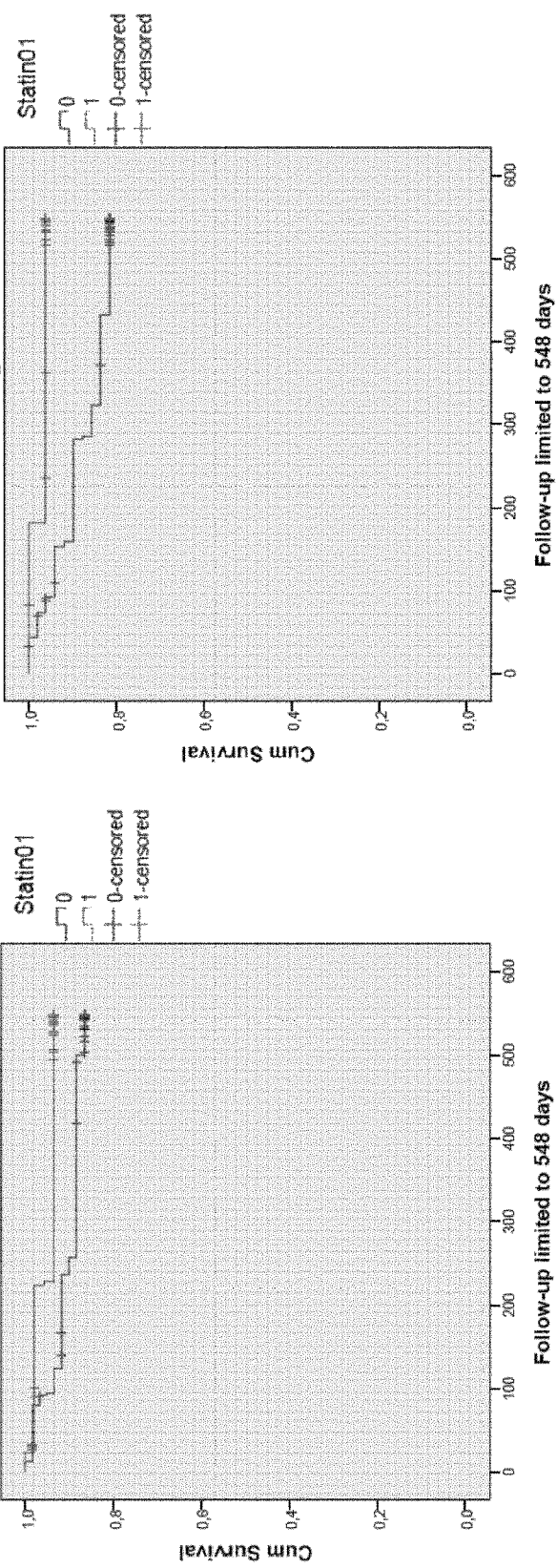
Figure 1:
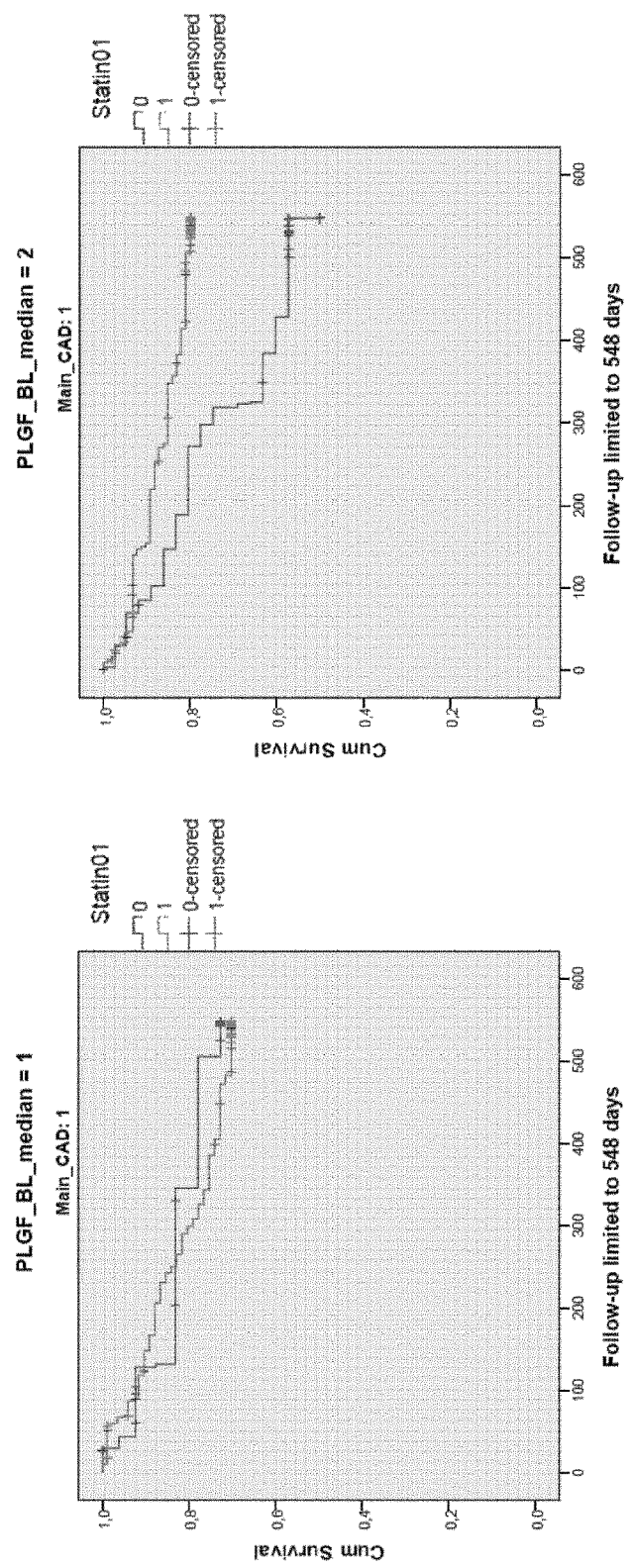
Figure 1:
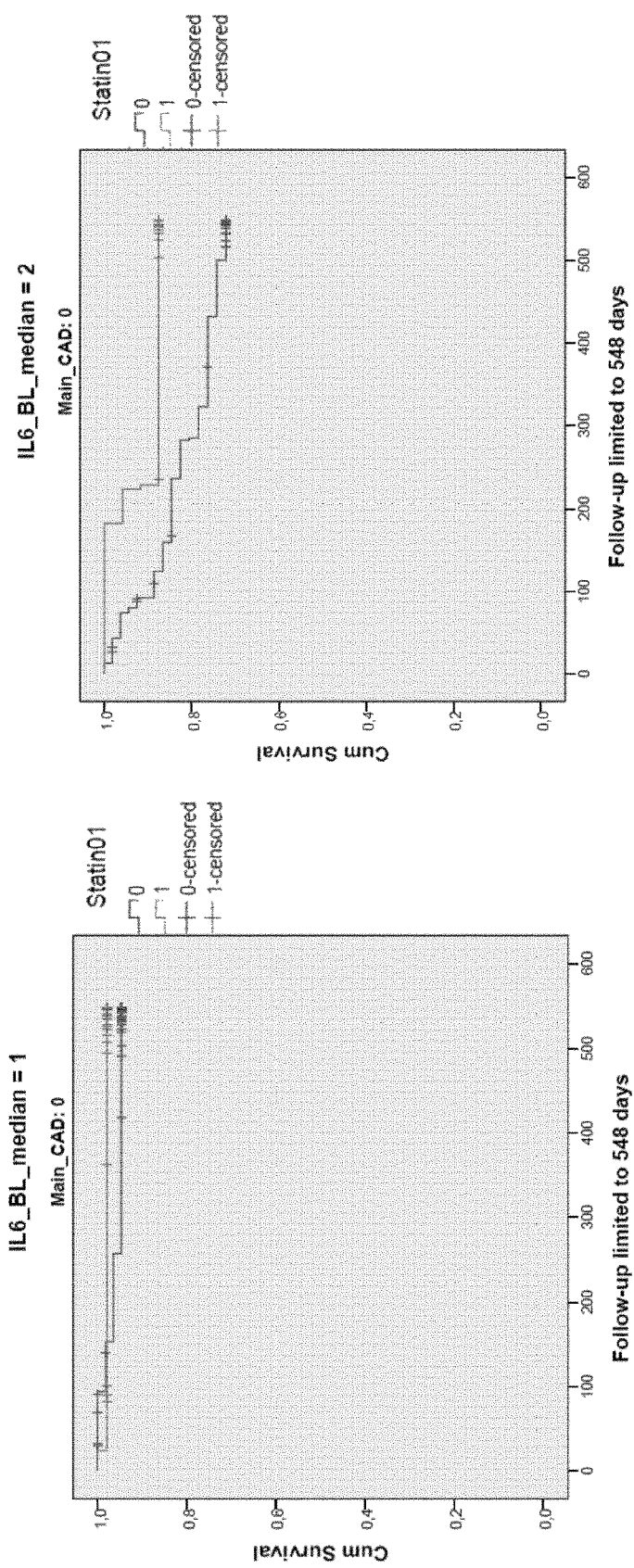
Figure 1:
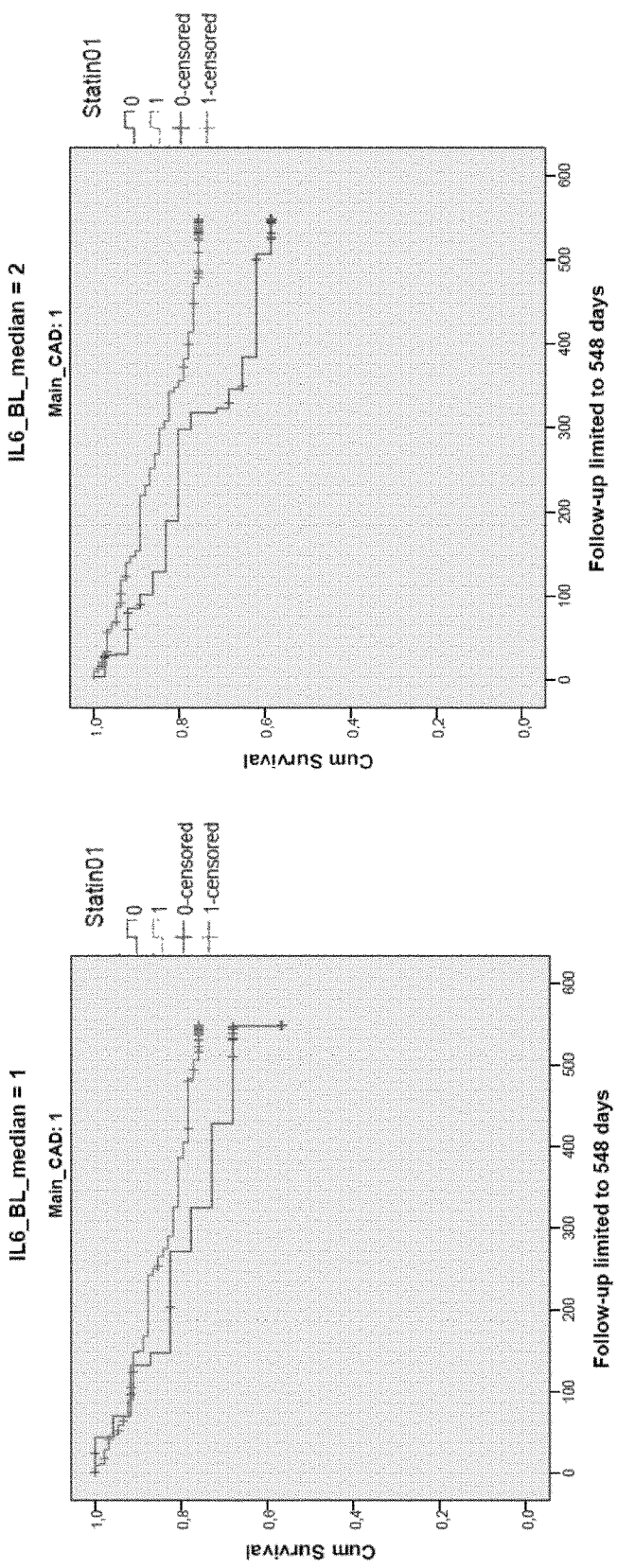
Figure 1:
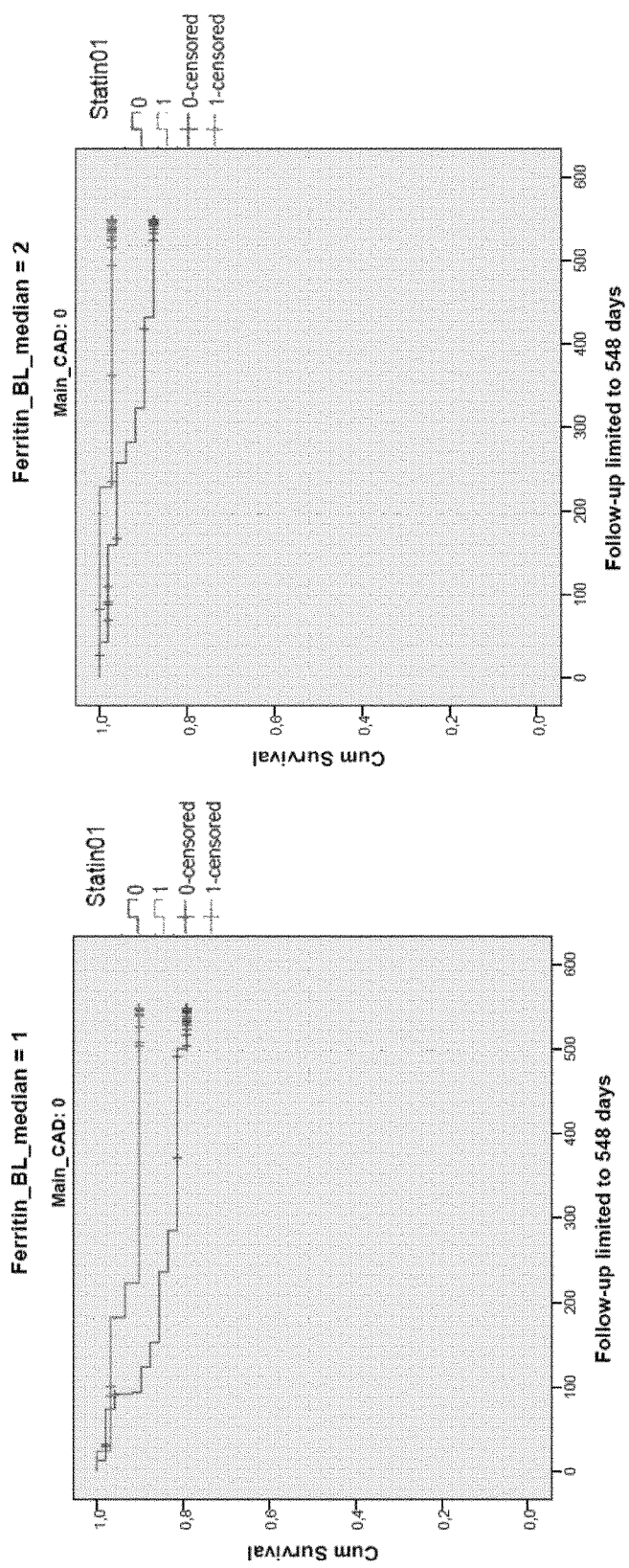
Figure 1:
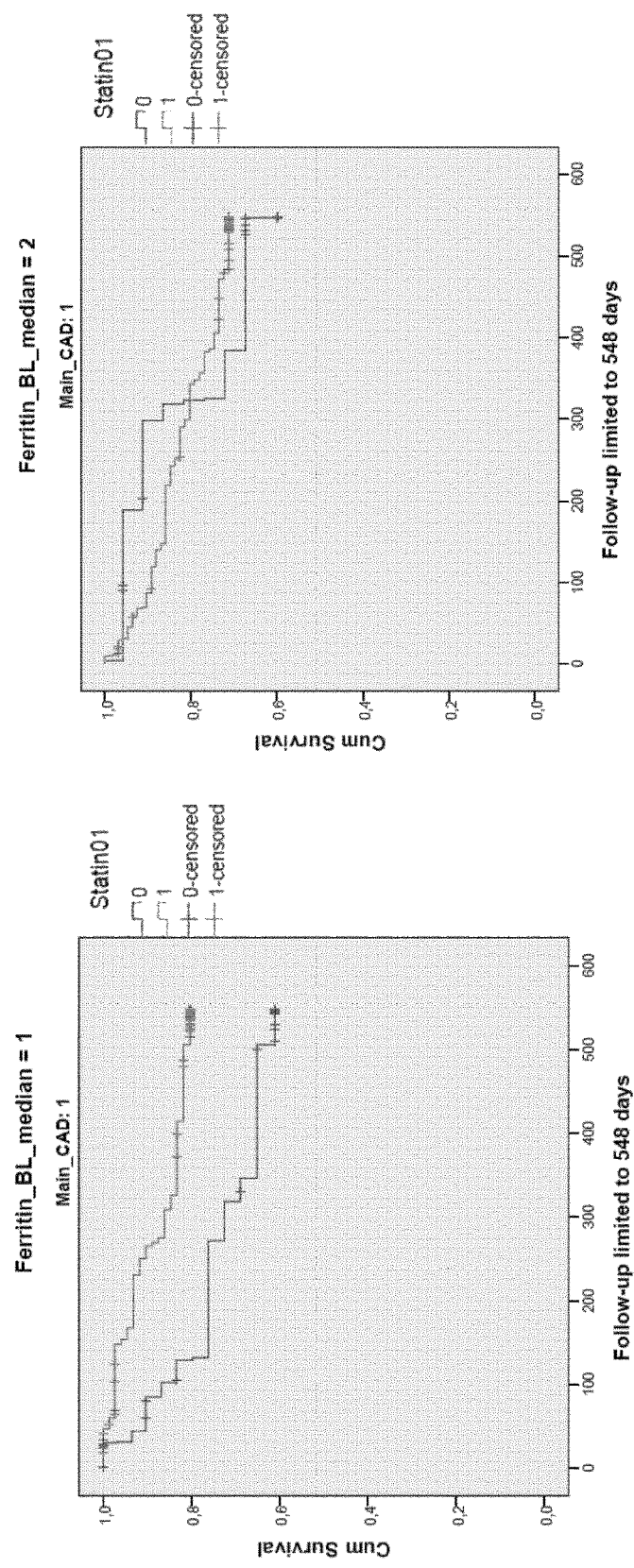
Figure 1:
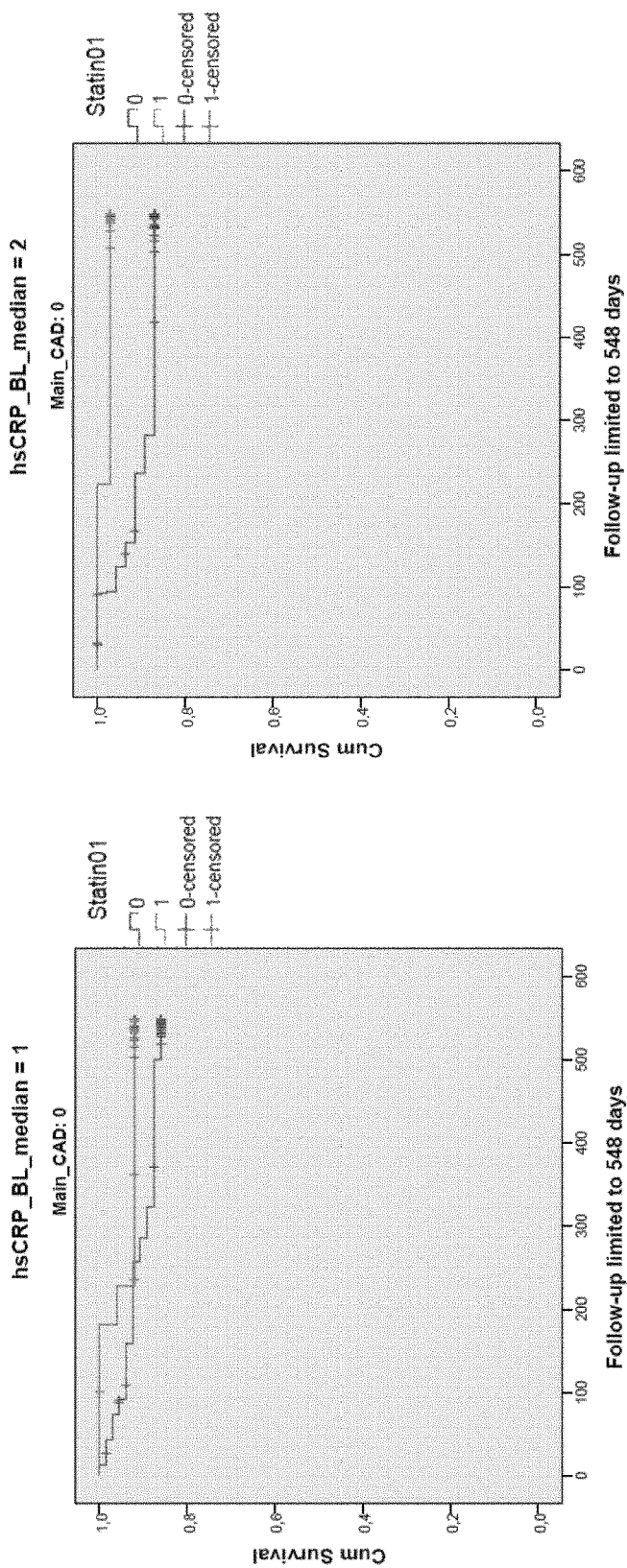
Figure 1:
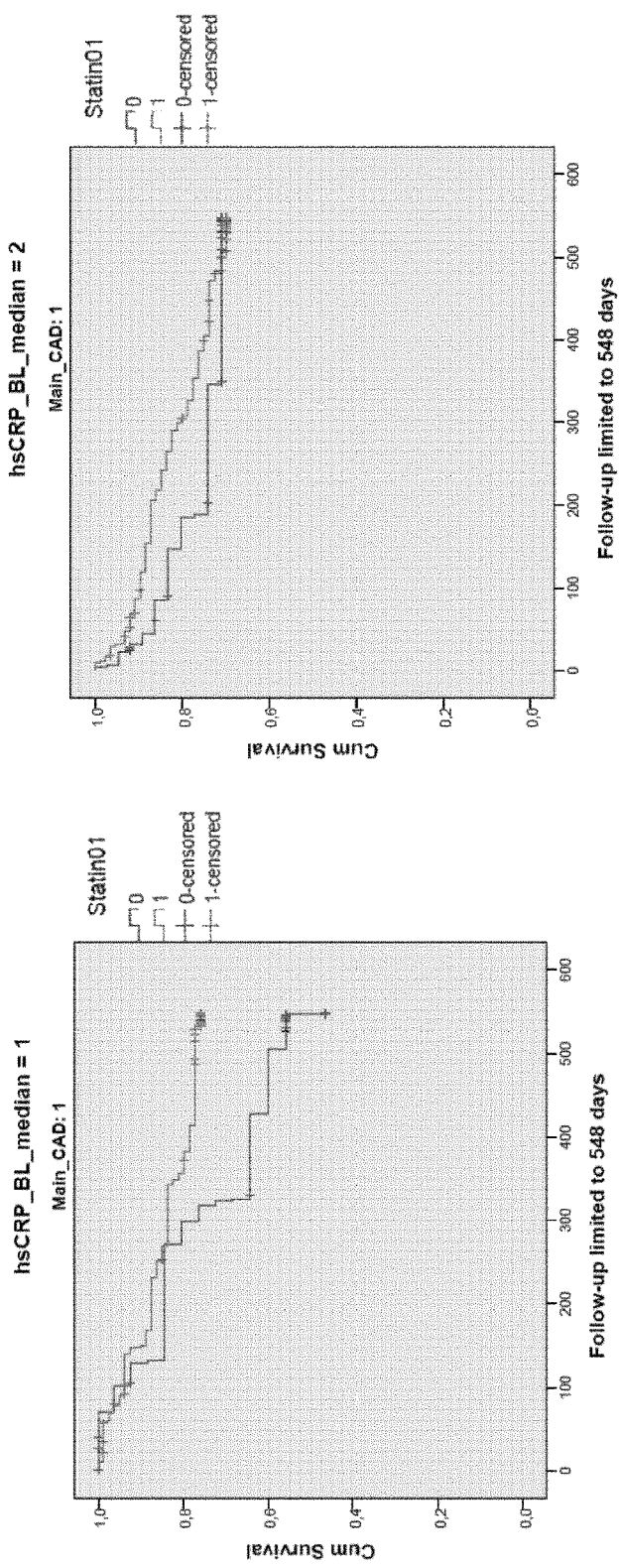
Figure 1:
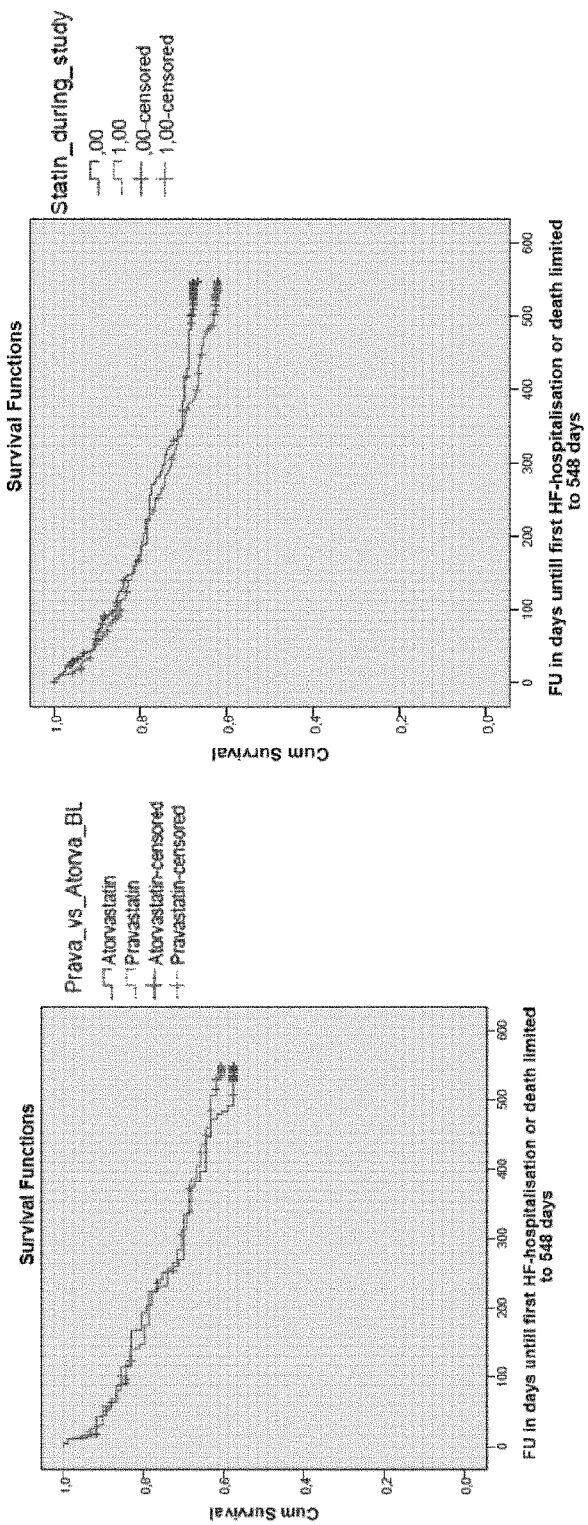

The present invention relates to a method of identifying a patient having heart failure as likely to respond to a therapy comprising a statin comprising:
(a) measuring a level of at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from the patient, and (b) comparing the level of the at least one biomarker to a respective reference level.

In an embodiment, the method further comprises step (c) of identifying a patient as more likely or less likely to respond to the therapy comprising statin when the level of the biomarker in the sample from the patient is (depending on the respective marker) above or below the reference level. Preferred diagnostic algorithms are disclosed elsewhere herein.

In a further embodiment, the method comprises step (d) of recommending, initiation or discontinuing a therapy comprising a statin.

In an embodiment, the level of the at least one biomarker is measured by contacting the sample with an agent that specifically binds to the respective marker, thereby forming a complex between the agent and said marker, detecting the amount of complex formed, and thereby measuring the level of said marker. This applies in particular, if the biomarker to be measured is a polypeptide (GDF-15, SHBG, PLGF IL-6 Transferrin, a cardiac Troponin, sFlt-1, Prealbumin, Ferritin, Osteopontin, sST2, and hsCRP).

If the biomarker is uric acid or urea, the level of said biomarker is, preferably, measured by contacting the sample with an enzyme of compound that allows for the conversion of said biomarker:

If the biomarker to be measured is uric acid, the level of said biomarker is, preferably, measured by contacting the sample with compound or enzyme that allows for the oxidation of uric acid. The enzyme preferably is an uricase (EC 1.7.3.3) which catalyzes the oxidation of uric acid to 5-hydroxyisourate. The compound, preferably, is phosphotungstic acid.

If the biomarker to be measured is urea, the level of said biomarker is, preferably, measured by contacting the sample with an urease (EC 3.5.1.5) which catalyzes the hydrolysis of urea into carbon dioxide and ammonia. In addition, the sample may be contacted thereafter with a glutamate dehydrogenase (EC 1.4.1.2). In the second reaction, 2-oxoglutarate reacts with ammonia in the presence of glutamate dehydrogenase (GLDH) and the coenzyme NADH to produce L-glutamate.

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison and/or assessment based on said comparison in step (b).

In the context of the method of the present invention, a patient shall be identified as likely to respond to a therapy comprising a statin, i.e. a therapy comprising the administration of a statin (or the administration of more than one statin). Preferably, the statin is administered orally.

Statins are well known in the art. Statins (frequently also referred to as "HMG-CoA reductase inhibitors") are a class of drugs used to lower cholesterol levels by inhibiting the enzyme HMG-CoA reductase, which plays a central role in the production of cholesterol in the liver. By inhibiting HMG-CoA reductase, statins block the pathway for synthesizing cholesterol in the liver. This is significant because most circulating cholesterol comes from internal manufacture rather than the diet.

Statins are divided into two groups, i) fermentation-derived and ii) synthetic. In the context of the present invention, the statins may be either synthetic or fermentation derived. A preferred statin is selected from the group consisting of Atorvastatin, Cerivastatin, Fluvastatin, Lovastatin, Mevastatin, Pitavastatin, Pravastatin, Rosuvastatin and Simvastatin. In a particularly preferred embodiment the statin is Atorvastatin or Pravastatin.

The phrase "identifying a patient" as used herein, preferably, refers to using the information or data generated relating to the level of the at least one marker as referred to herein in a sample of a patient to identify or selecting the patient as more likely to benefit or less likely to benefit from a therapy comprising a statin. In particular, a patient is considered to respond to a therapy comprising a statin (and, thus, to be more likely to benefit from said therapy), if said therapy reduces the risk of mortality of said patient and/or reduces the risk of hospitalization of said patient, preferably, within a window period of 18 months or 3 years after the sample to be tested has been obtained. Preferably, the aforementioned risk (or risks) is (are) reduced by at least 5%, more preferably by at least 10%, and, most preferably by at least 20%. Also, a patient is considered not to respond to a therapy comprising a statin (and, thus, to be more likely not to benefit from said therapy), if said therapy does not reduce the risk of mortality and/or hospitalization, in particular does not reduce significantly the risk of mortality and/or hospitalization of said patient, preferably, within a window period of 18 months or 3 years after the sample to be tested has been obtained. In this case, unnecessary health care costs can be avoided, if the medicament is not administered. Further, adverse side effects that may result from the therapy comprising a statin can be avoided.

The terms "mortality" and "hospitalization" are defined elsewhere herein.

The information or data used or generated for the identification may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of the at least one marker to a reference level. In some embodiments, the information or data includes an indication that the patient is more likely or less likely to respond to a therapy comprising a statin.

The terms "less likely" and "more likely" are understood by the skilled person. A patient who is more likely to respond to a therapy comprising a statin has an elevated probability, in particular a significantly elevated probability to respond to said therapy as compared the average probability in population of patients, whereas a patient who is less likely to respond to a therapy comprising a statin has a reduced probability, in particular a significantly reduced probability to respond to said therapy as compared the average probability in population of patients. Preferably, the population of patients shows the same characteristics. In particular, it is envisaged that the patients comprised by the population have heart failure. Moreover, the patients may or may not suffer from coronary artery disease as specified elsewhere herein (which may depend on the biomarker to be measured). An elevated probability means that the probability is preferably elevated by at least 10%, more preferably, by at least 20% or 30%, and most preferably by at least 40% as compared to the average probability in a population of patients. A reduced probability means that the probability is preferably reduced by at least 10%, more preferably, by at least 20% or 30%, and most preferably by at least 40% as compared to the average probability in a population of patients.

As will be understood by those skilled in the art, the assessment whether a patient is likely to respond to a therapy comprising a statin is usually not intended to be correct for 100% of the patients to be assessed. The term, however, requires that the assessment is correct for a statistically significant portion of the patients (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the patients of a population can be properly identified by the method of the present invention.

The terms "patient" and "subject" are used interchangeably herein. The terms as used herein in the context with the aforementioned method relates to animals, preferably mammals, and, more preferably, humans. A "patient" or "subject" herein, preferably, is any single human subject eligible for treatment who is experiencing or has experienced one or more signs, symptoms, or other indicators of heart failure. Intended to be included as a subject are any subjects involved in clinical research trials, or subjects involved in epidemiological studies, or subjects once used as controls. The patient may have been previously treated with a statin, or not. Accordingly, the patient to be tested may have been treated with a statin prior to obtaining the sample to be tested, or may not have been treated with a statin prior to obtaining the sample.

It is envisaged in the context of the present invention, that the patient suffers from heart failure (HF), in particular from symptomatic heart failure.

The term "heart failure" as used herein relates to an impaired systolic and/or diastolic function of the heart being accompanied by overt signs of heart failure as known to the person skilled in the art. Preferably, heart failure referred to herein is also chronic heart failure. Heart failure according to the present invention includes overt and/or advanced heart failure. In overt heart failure, the patient shows symptoms of heart failure as known to the person skilled in the art.

HF can be classified into various degrees of severity.

According to the NYHA (New York Heart Association) classification, heart failure patients are classified as belonging to NYHA classes I, II, III and IV. A patient having heart failure has already experienced structural and functional changes to his pericardium, myocardium, coronary circulation or cardiac valves. He will not be able to fully restore his health, and is in need of a therapeutical treatment. Patients of NYHA Class I have no obvious symptoms of cardiovascular disease but already have objective evidence of functional impairment. Patients of NYHA class II have slight limitation of physical activity. Patients of NYHA class III show a marked limitation of physical activity. Patients of NYHA class IV are unable to carry out any physical activity without discomfort. They show symptoms of cardiac insufficiency at rest.

This functional classification is supplemented by the more recent classification by the American College of Cardiology and the American Heart Association (ACC/AHA classification, see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy and/or impaired LV function would be designated as stage B. Stage C then denotes patients with current or past symptoms of HF associated with underlying structural heart disease (the bulk of patients with HF), and stage D designates patients with truly refractory HF.

As used herein, the term "heart failure", in particular, refers to stages B, C and D of the ACC/AHA classification referred to above. In these stages, the patient shows typical symptoms of heart failure and/or shows structural and/or functional abnormalities of the heart. Accordingly, a patient who suffers from heart failure, suffers from heart failure classified as stage B, C or D according to the ACC/AHA classification. Also preferably, the patient suffers from heart failure classified as NYHA class II; III or IV. In a preferred embodiment, the term "heart failure" refers to stages B and C of the ACC/AHA classification referred to above, or to heart failure classified as NYHA class II or class III. Accordingly, the patient preferably suffers from heart failure classified as stage B or C according to the ACC/AHA classification. Also preferably, the patient suffers from heart failure classified as NYHA class II or III.

In addition to heart failure, the patient may or may not suffer from coronary artery disease depending on the biomarker to be measured:

If the biomarker is transferrin or ferritin the patient preferably suffers from heart failure and coronary artery disease.

If the biomarker is osteopontin or sST2, the patient suffers from heart failure, but preferably does not suffer from coronary artery disease.

If the biomarker GDF-15, urea, uric acid, a cardiac Troponin, SHBG, prealbumin, PlGF, sFlt-1, IL-6, or hsCRP the patient may or may not suffer from coronary artery. However, in case the biomarker is urea, uric acid, sFlt-1, PlGF or IL-6, it is preferred that the patient also suffers from CAD.

The term "coronary artery disease", abbreviated CAD, frequently also called coronary heart disease (CHD) or atherosclerotic heart disease, is known to the person skilled in the art. Preferably, the term refers to a condition in which the blood vessels that supply blood and oxygen to the heart are narrowed. Coronary artery disease is usually caused by a condition called atherosclerosis, which occurs when fatty material and a substance called plaque builds up on the walls of your arteries. This causes their lumen to get narrow. Particularly, CAD is the result of the accumulation of atheromatous plaques within the walls of the arteries that supply the myocardium (the muscle of the heart). Preferably, a patient with stable CAD has at least 50% stenosis (and thus at least 50% occlusion), in at least one major coronary artery.

How to assess the degree of occlusion of a coronary artery is well known in the art, preferably, the degree is assessed by coronary angiography. While the symptoms and signs of coronary artery disease are noted in the advanced state of disease, many individuals with coronary artery disease show no evidence of disease for decades as the disease progresses before the first onset of symptoms of an acute event, often a "sudden" heart attack, finally arise.

If the patient has also coronary artery disease, it is in particular contemplated that the patient has stable coronary artery disease. The term "stable" in this context means, that the patient does not suffer from ACS (acute coronary syndrome), in particular at the time at which the sample to be tested has been obtained. The term "ACS" is well known in the art and includes STEMI (ST-elevation myocardial infarction); NSTEMI (non ST-elevation myocardial infarction) and unstable angina pectoris. It is further envisaged that the patient to be tested does not have a recent history of ACS, and thus shall not have suffered from ACS recently. In particular, the patient shall not have suffered from ACS within one month prior to carrying out the method of the present invention (to be more precise, within one month prior to obtaining the sample).

Preferably, the patient in the context of the present invention does not have impaired renal function. Preferably, the patient shall not suffer from renal failure, in particular the patient shall not suffer from acute, chronic and/or end stage renal failure. Further, the patient, preferably, shall not suffer from renal hypertension. How to assess whether a patient exhibits impaired renal function is well known in the art. Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. All calculations derived from formulas such as the Cockgroft Gault formula of the MDRD formula deliver estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min). The normal range of GFR for males is 97 to 137 mL/min, the normal range of GFR for females is 88 to 128 ml/min. Thus, it is particularly contemplated that the GFR of a patient who does not exhibit impaired renal function is within this range. Moreover, said subject preferably, has a blood creatinine level (in particular a serum creatinine level) of lower than 0.9 mg/dl, more preferably of lower than 1.1 mg/dl and most preferably of lower than 1.3 mg/dl.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, bronchial lavage or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

In a preferred embodiment of the present invention, the sample is a blood, blood serum or blood plasma sample. It is, in particular, contemplated to measure the level of the biomarker in a plasma sample.

In the context of the present invention, the level of at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) is measured in a sample from the patient. Thus, the level of a single biomarker can be measured, or the levels of a combination of biomarkers.

In a preferred embodiment, the level of at least one biomarker selected from the group consisting of GDF-15, Urea, SHBG, PLGF, or IL-6 is measured.

In the following, definitions for the biomarkers to be used in the context of the present invention are given.

The term "Growth-Differentiation Factor-15" or "GDF-15" relates to a polypeptide being a member of the transforming growth factor (TGF) cytokine superfamily. The terms polypeptide, peptide and protein are used interchangeable throughout this specification. GDF-15 was originally cloned as macrophage-inhibitory cytokine 1 and later also identified as placental transforming growth factor-15, placental bone morphogenetic protein, non-steroidal anti-inflammatory drug-activated gene 1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-related cytokines, GDF-15 is synthesized as an inactive precursor protein, which undergoes disulfide-linked homodimerization. Upon proteolytic cleavage of the N terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses also variants of the aforementioned specific GDF-15 polypeptides. Such variants have at least the same essential biological and immunological properties as the specific GDF-15 polypeptides. In particular, they share the same essential biological and immunological properties if they are detectable by the same specific assays referred to in this specification, e.g., by ELISA assays using polyclonal or monoclonal antibodies specifically recognizing the said GDF-15 polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific GDF-15 polypeptides, preferably with the amino acid sequence of human GDF-15, more preferably over the entire length of the specific GDF-15, e.g. of human GDF-15. The degree of identity between two amino acid sequences can be determined as described above. Variants referred to above may be allelic variants or any other species specific homologs, paralogs, or orthologs. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to posttranslational modifications such as phosphorylation or myristylation.

The term "cardiac Troponin" encompasses also variants of the aforementioned specific Troponins, i.e., preferably, of Troponin I, and more preferably, of Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific Troponin. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Preferably, the cardiac troponin variants have immunological properties (i.e. epitope composition) comparable to those of human troponin T or troponin I. Thus, the variants shall be recognizable by the aforementioned means or ligands used for determination of the concentration of the cardiac troponins. Thus, the variants shall be recognizable by the aforementioned means or ligands used for determination of the concentration of the cardiac troponins. Such fragments may be, e.g., degradation products of the Troponins. Further included are variants which differ due to posttranslational modifications such as phosphorylation or myristylation. Preferably the biological property of troponin I and its variant is the ability to inhibit actomyosin ATPase or to inhibit angiogenesis in vivo and in vitro, which may e.g. be detected based on the assay described by Moses et al. 1999 PNAS USA 96 (6): 2645-2650). Preferably the biological property of troponin T and its variant is the ability to form a complex with troponin C and I, to bind calcium ions or to bind to tropomyosin, preferably if present as a complex of troponin C, I and T or a complex formed by troponin C, troponin I and a variant of troponin T. It is known that low concentrations of circulating cardiac troponin may be detected in subjects at various conditions, but further studies are required to understand their respective role and rate (Masson et al., Curr Heart Fail Rep (2010) 7:15-21).

Osteopontin (OPN), also known as bone sialoprotein I (BSP-1 or BNSP), early T-lymphocyte activation (ETA-1), secreted phosphoprotein 1 (SPP1), 2ar and Rickettsia resistance (Ric), is a polypeptide which is a highly negatively charged, extracellular matrix protein that lacks an extensive secondary structure. It is composed of about 300 amino acids (297 in mouse; 314 in human) and is expressed as a 33-kDa nascent protein; there are also functionally important cleavage sites. OPN can go through posttranslational modifications which increase its apparent molecular weight to about 44 kDa. The sequence of osteopontin is well known in the art (human osteopontin: UniProt P10451, GenBank NP_000573.1) Osteopontin is found in normal plasma, urine, milk and bile (U.S. Pat. No. 6,414,219; U.S. Pat. No. 5,695,761; Denhardt, D. T. and Guo, X., FASEB J. 7 (1993) 1475-1482; Oldberg, A., et al., PNAS 83 (1986) 8819-8823; Oldberg, A., et al., J. Biol. Chem. 263 (1988) 19433-19436; Giachelli, C M., et al., Trends Cardiovasc. Med. 5 (1995) 88-95). The human OPN protein and cDNA have been isolated and sequenced (Kiefer M. C, et al., Nucl. Acids Res. 17 (1989) 3306). OPN functions in cell adhesion, chemotaxis, macrophage-directed interleukin-10. OPN is known to interact with a number of integrin receptors. Increased OPN expression has been reported in a number of human cancers, and its cognate receptors (av-b3, av-b5, and av-b1 integrins and CD44) have been identified. In vitro studies by Irby, R. B., et al., Clin. Exp. Metastasis 21 (2004) 515-523 indicate that both endogenous OPN expression (via stable transfection) as well as exogenous OPN (added to culture medium) enhanced the motility and invasive capacity of human colon cancer cells in vitro.

The term "soluble Flt-1" or "sFlt-1" as used herein refers to polypeptide which is a soluble form of the VEGF receptor Flt1. It was identified in conditioned culture medium of human umbilical vein endothelial cells. The endogenous soluble Flt1 (sFlt1) receptor is chromatographically and immunologically similar to recombinant human sFlt1 and binds [125I] VEGF with a comparable high affinity. Human sFlt1 is shown to form a VEGF-stabilized complex with the extracellular domain of KDR/Flk-1 in vitro. Preferably, sFlt1 refers to human sFlt1. More preferably, human sFlt1 can be deduced from the amino acid sequence of Flt-1 as shown in Genbank accession number P17948, GI: 125361. An amino acid sequence for mouse sFlt1 is shown in Genbank accession number BAA24499.1, GI: 2809071.

The term "sFlt-1" used herein also encompasses variants of the aforementioned specific sFlt-1 polypeptide. Such variants have at least the same essential biological and immunological properties as the specific sFlt-1 polypeptide. In particular, they share the same essential biological and immunological properties if they are detectable by the same specific assays referred to in this specification, e.g., by ELISA assays using polyclonal or monoclonal antibodies specifically recognizing the said sFlt-1 polypeptide. For a more detailed explanation of the term "variants", please see above.

The term "PlGF" (Placental Growth Factor) as used herein refers to a placenta derived growth factor which is a 149-amino-acid-long polypeptide and is highly homologous (53% identity) to the platelet-derived growth factor-like region of human vascular endothelial growth factor (VEGF). Like VEGF, PlGF has angiogenic activity in vitro and in vivo. For example, biochemical and functional characterization of PlGF derived from transfected COS-1 cells revealed that it is a glycosylated dimeric secreted protein able to stimulate endothelial cell growth in vitro (Maqlione 1993, Oncogene 8(4):925-31). Preferably, PlGF refers to human PlGF, more preferably, to human PlGF having an amino acid sequence as shown in Genbank accession number P49763, GI: 17380553.

ST2, frequently also referred to as "Interleukin 1 receptor-like 1", is a member of the IL-1 receptor family that is produced by cardiac fibroblasts and cardiomyocytes under conditions of mechanical stress. ST2 is an interleukin-1 receptor family member and exists in both membrane-bound isoform and a soluble isoform (sST2). In the context of the present invention, the amount of soluble ST2 shall be determined (see Dieplinger et al. (Clinical Biochemistry, 43, 2010: 1169 to 1170). ST2 also known as Interleukin 1 receptor-like 1 or IL1RL1, is encoded in humans by the IL1RL1 gene. The sequence of the human ST2 polypeptide is well known in the art, and e.g. accessible via GenBank, see NP_003847.2 GI:27894328. Soluble ST2 (sST2) is believed to function as a decoy receptor by binding IL-33 and abrogating the otherwise cardioprotective effect of IL-33 signaling through the cell membrane-bound form of ST2.

Interleukin-6 (abbreviated as IL-6) is an interleukin is secreted by T cells and macrophages to stimulate immune response, e.g. during infection and after trauma, especially burns or other tissue damage leading to inflammation. It acts as both a pro-inflammatory and anti-inflammatory cytokine. In humans, it is encoded by the IL6 gene. The sequence of human IL-6 can be assessed via GenBank (see NM_000600.3 for the polynucleotide sequence, and NP_000591.1 for the amino acid sequence). IL-6 signals through a cell-surface type I cytokine receptor complex consisting of the ligand-binding IL-6Rα chain (CD126), and the signal-transducing component gp130 (also called CD130). CD130 is the common signal transducer for several cytokines including leukemia inhibitory factor (LIF), ciliary neurotropic factor, oncostatin M, IL-11 and cardiotrophin-1, and is almost ubiquitously expressed in most tissues. In contrast, the expression of CD126 is restricted to certain tissues. As IL-6 interacts with its receptor, it triggers the gp130 and IL-6R proteins to form a complex, thus activating the receptor. These complexes bring together the intracellular regions of gp130 to initiate a signal transduction cascade through certain transcription factors, Janus kinases (JAKs) and Signal Transducers and Activators of Transcription.

CRP, herein also referred to as C-reactive protein, is an acute phase protein that was discovered more than 75 years ago to be a blood protein that binds to the C-polysaccharide of pneumococci. CRP is known as a reactive inflammatory marker and is produced by a distal organ (i.e. the liver) in response or reaction to chemokines or interleukins originating from the primary lesion site. CRP consists of five single subunits, which are non covalently linked and assembled as a cyclic pentamer with a molecular weight of approximately 110-140 kDa. Preferably, CRP as used herein relates to human CRP. The sequence of human CRP is well known and disclosed, e.g., by Woo et al. (J. Biol. Chem. 1985. 260 (24), 13384-13388). The level of CRP is usually low in normal individuals but can rise 100- to 200-fold or higher due to inflammation, infection or injury (Yeh (2004) Circulation. 2004; 109:II-11-II-14). It is known that CRP is an independent factor for the prediction of a cardiovascular risk. Particularly, it has been shown that CRP is suitable as a predictor for myocardial infarction, stroke, peripheral arterial disease and sudden cardiac death. Moreover, elevated CRP amounts may also predict recurrent ischemia and death in patients with acute coronary syndrome (ACS) and those undergoing coronary intervention. Determination of CRP is recommended by expert panels (e.g. by the American Heart Association) in patients with a risk of coronary heart disease (see also Pearson et al. (2003) Markers of Inflammation and Cardiovascular Disease. Circulation, 107: 499-511). The term CRP also relates to variants thereof.

Preferably, the amount of CRP in a sample of a patient is determined by using CRP assays with a high sensitivity. The CRP determined by such assays is frequently also referred to as high sensitivity CRP (hsCRP). hsCRP assays are, e.g., used to predict the risk of heart disease. Suitable hsCRP assays are known in the art. A particularly preferred hsCRP assay in the context of the present invention is the Roche/Hitachi CRP (Latex) HS test with a detection limit of 0.1 mg/l.

Ferritin is an iron storage protein. Ferritin is a macromolecule with a molecular weight of at least 440 kDa, depending on the iron content, and consists of a protein shell (apoferritin) of 24 subunits and an iron core containing an average of approximately 2500 $Fe^{3+}$ ions (in liver and spleen ferritin). In vertebrates, these subunits are both the light (L) and the heavy (H) type with an apparent molecular weight of 19 kDA or 21 kDA respectively. Ferritin tends to form oligomers. At least 20 isoferritins can be distinguished with the aid of ioselectric focusing. This microheterogeneity is due to differences in the contents of the acidic H and weakly basic L subunits. The basic isoferritins are responsible for the long-term iron storage function, and are mainly found in liver, spleen and bone marrow.

Prealbumin is a tryptophan-rich protein which is synthesized in hepatocytes and has a molar mass of 55 kDa. At a pH of 8.6, an electrophoretic band appears prior to albumin in a relative amount of <2.5% due to its greater rate of diffusion to the anode. Its function is to bind and transport low molecular weight retinol-binding proteins (molar mass of less than 21 kDa), preventing their glomerular filtration. 30-50% of circulating prealbumin is complexed by retinol-binding protein. Furthermore, it binds and transports thyroxine (T4). Frequently, prealbumin is also referred to as Transthyretin.

Sex hormone-binding globulin (SHBG) is the blood transport protein for testosterone and estradiol. It is a large glycoprotein with a molecular weight of about 95 kD, and exists as a homodimer composed of two identical subunits. Each subunit contains two disulfide bridges. SHBG is produced mostly by the liver and is released into the bloodstream. Other sites that produce SHBG include the brain, uterus, testes, and placenta. The sequence of SHBG is well known in the art, see e.g. GenBank Accession No. NP_001031.2 GI:7382460).

Transferrin is a glycoprotein with a molecular weight of about 80 kDa. It comprises a polypeptide strand with two N-glycosidically linked oligosaccharide chains and exists in numerous isoforms. The rate of synthesis in the liver can be altered in accordance with the body's iron requirements and iron reserves. Transferrin is the iron transport protein in serum. In cases of iron deficiency, the degree of transferrin saturation appears to be an extremely sensitive indicator of functional iron depletion. A variety of methods are available for determining transferrin including radial immunodiffusion, nephelometry and turbidimetry.

In the context of the method of the present invention it is, in particular, envisaged that the amounts of human peptides or polypeptides are determined.

Uric acid is the final product of purine metabolism in a subject organism. The IUPAC name is 7,9-dihydro-3H-purine-2,6,8-trione. The compound is frequently also referred to as urate, Lithic acid, 2,6,8-trioxypurine, 2,6,8-trihydroxypurine, 2,6,8-Trioxopurine, 1H-Purine-2,6,8-triol (compound formula $C_5H_4N_4O_3$, PubChem CID 1175, CAS number 69-93-2).

Uric acid measurements are used in the diagnosis and treatment of numerous renal and metabolic disorders, including renal failure, gout, leukemia, psoriasis, starvation or other wasting conditions, and of patients receiving cytotoxic drugs. The oxidation of uric acid provides the basis for two approaches to the quantitative determination of this purine metabolite. One approach is the reduction of phosphotungstic acid in an alkaline solution to tungsten blue, which is measured photometrically. A second approach, described by Praetorius and Poulson, utilizes the enzyme uricase to oxidize uric acid; this method eliminates the interferences intrinsic to chemical oxidation (Praetorius E, Poulsen H. Enzymatic Determination of Uric Acid with Detailed Directions. Scandinav J Clin Lab Investigation 1953; 3:273-280). Uricase can be employed in methods that involve the UV measurement of the consumption of uric acid or in combination with other enzymes to provide a colorimetric assay. Another method is the colorimetric method developed by Town et al. (Town M H, Gehm S, Hammer B, Ziegenhorn J. J Clin Chem Clin Biochem 1985; 23:591) The sample is initially incubated with a reagent mixture containing ascorbate oxidase and a clearing system. In this test system it is important that any ascorbic acid present in the sample is eliminated in the preliminary reaction; this precludes any ascorbic acid interference with the subsequent POD indicator reaction. Upon addition of the starter reagent, oxidation of uric acid by uricase begins.

In the context of the present invention, uric acid can be determined by any method deemed appropriate. Preferably, the biomarker is determined by the aforementioned methods. More preferably, uric acid is determined by applying a slight modification of the colorimetric method described above. In this reaction, the peroxide reacts in the presence of peroxidase (POD), N-ethyl-N-(2-hydroxy-3-sulfopropyl)-3-methylaniline (TOOS), and 4-aminophenazone to form a quinone-diimine dye. The intensity of the red color formed is proportional to the uric acid concentration and is determined photometrically.

Urea is the major end product of protein nitrogen metabolism. It has the chemical formula $CO(NH_2)_2$ and is synthesized by the urea cycle in the liver from ammonia which is produced by amino acid deamination. Urea is excreted mostly by the kidneys but minimal amounts are also excreted in sweat and degraded in the intestines by bacterial action. Determination of blood urea nitrogen is the most widely used screening test for renal function.

The term "measuring" the level of a biomarker, as used herein refers to the quantification of the biomarker, e.g. to determining the level of the biomarker in the sample, employing appropriate methods of detection described elsewhere herein. The terms "measuring", "detecting" and "determining" are used interchangeably herein.

The biomarkers as referred to herein can be detected using methods generally known in the art. Methods of detection generally encompass methods to quantify the level of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RI-As, fluorescence-based immunoassays, which are commercially available. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used immunoassays.

Methods for measuring electrochemiluminescent phenomena are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

Biomarkers can also be detected by generally known methods including magnetic resonance spectroscopy (NMR spectroscopy), Gas chromatography-mass spectrometry (GC-MS), Liquid chromatography-mass spectrometry (LC-MS), High and ultra-HPLC HPLC such as reverse phase HPLC, for example, ion-pairing HPLC with dual UV-wavelength detection, capillary electrophoresis with laser-induced fluorescence detection, anion exchange chromatography and fluorescent detection, thin layer chromatography.

Preferably, measuring the level of a peptide or polypeptide comprises the steps of (a) contacting a cell capable of eliciting a cellular response the intensity of which is indicative of the level of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the level of the peptide or polypeptide.

Also preferably, measuring the level of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Measuring the level of a peptide or polypeptide may, preferably, comprises the steps of (a) contacting the peptide with a specific binding agent, (b) (optionally) removing non-bound binding agent, (c) measuring the level of bound binding agent, i.e. the complex of the binding agent formed in step (a). According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound binding agent, i.e. the binding agent or the binding agent/peptide complex, will generate an intensity signal. Binding according to the present invention includes both covalent and non-covalent binding. A binding agent according to the present invention can be any compound, e.g., a peptide, polypeptide, nucleic acid, or small molecule, binding to the peptide or polypeptide described herein. Preferred binding agents include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such binding agents are well-known in the art. For example, identification and production of suitable antibodies or aptamers is also offered by commercial suppliers. The person skilled in the art is familiar with methods to develop derivatives of such binding agents with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the binding agent or agent binds specifically to the pep-tide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the binding agent can be measured by any method known in the art. Preferably, said method is semi-quantitative or quantitative. Further suitable techniques for the determination of a polypeptide or peptide are de-scribed in the following.

Binding of a binding agent may be measured directly, e.g. by NMR or surface plasmon resonance. Measurement of the binding of a binding agent, according to preferred embodiments, is performed by an analyzer unit of a system disclosed herein. Thereafter, an level of the measured binding may be calculated by a computing device of a system disclosed herein. If the binding agent also serves as a substrate of an enzymatic activity of the pep-tide or polypeptide of interest, an enzymatic reaction product may be measured (e.g. the level of a protease can be measured by measuring the level of cleaved substrate, e.g. on a Western Blot). Alternatively, the binding agent may exhibit enzymatic properties itself and the "binding agent/peptide or polypeptide" complex or the binding agent which was bound by the peptide or polypeptide, respectively, may be contacted with a suitable substrate allowing detection by the generation of an intensity signal. For measurement of enzymatic reaction products, preferably the level of substrate is saturating. The substrate may also be labeled with a detectable lable prior to the reaction. Preferably, the sample is contacted with the substrate for an adequate period of time. An adequate period of time refers to the time necessary for an detectable, preferably measurable, level of product to be produced. Instead of measuring the level of product, the time necessary for appearance of a given (e.g. detectable) level of product can be measured. Third, the binding agent may be coupled covalently or non-covalently to a label allowing detection and measurement of the binding agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent. The use of secondary, tertiary or even higher order binding agents is often used to increase the signal. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Glutathion-S-Transferase, FLAG, GFP, myc-tag, influenza A virus hae-magglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluo-rescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The level of a peptide or polypeptide may be, also preferably, determined as follows: (a) contacting a solid support comprising a binding agent for the peptide or polypeptide as specified above with a sample comprising the peptide or polypeptide and (b) measuring the level peptide or polypeptide which is bound to the support. The binding agent, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The binding agent or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said binding agent are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different binding agents. Methods of producing such arrays, for example based on solid-phase chemistry and photo-labile protective groups, are generally known (U.S. Pat. No. 5,744,305).

In an embodiment of the method of the present invention, the levels of the biomarkers as referred to herein are measured by using the assays described in the Examples section.

In another embodiment of the method of the present invention, the measurement in step a) may be carried out by an analyzer unit, in particular by an analyzer unit as defined elsewhere herein.

The term "binding agent" refers to a molecule that comprises a binding moiety which specifically binds the corresponding to the respective biomarker.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule. Preferably, the level of binding to a molecule other than the target molecule results in a binding affinity which is only 10% or less, more preferably only 5% or less of the affinity to the target molecule.

Examples of "binding agents" are a nucleic acid probe, nucleic acid primer, DNA molecule, RNA molecule, aptamer, antibody, antibody fragment, peptide, peptide nucleic acid (PNA) or chemical compound. A preferred binding agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Preferably, the antibody is a polyclonal antibody. More preferably, the antibody is a monoclonal antibody.

Another binding agent that can be applied, in an aspect, may be an aptamere which specifically binds to the at least one marker in the sample. The term "specific binding" or "specifically binds", when referring to a nucleic acid aptamer as a binding agent, refers to a binding reaction wherein a nucleic acid aptamer binds to the corresponding target molecule with an affinity in the low nM to pM range.

In yet an aspect the, sample is removed from the complex formed between the binding agent and the at least one marker prior to the measurement of the amount of formed complex. Accordingly, in an aspect, the binding agent may be immobilized on a solid support. In yet an aspect, the sample can be removed from the formed complex on the solid support by applying a washing solution. The formed complex shall be proportional to the amount of the at least one marker present in the sample. It will be understood that the specificity and/or sensitivity of the binding agent to be applied defines the degree of proportion of at least one marker comprised in the sample which is capable of being specifically bound. Further details on how the determination can be carried out are also found elsewhere herein. The amount of formed complex shall be transformed into an amount of at least one marker reflecting the amount indeed present in the sample. Such an amount, in an aspect, may be essentially the amount present in the sample or may be, in another aspect, an amount which is a certain proportion thereof due to the relationship between the formed complex and the amount present in the original sample.

The term "level" as used herein encompasses the absolute amount of a biomarker as referred to herein, the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the level of the biomarker in the sample from the individual or patient with the reference level of the biomarker specified elsewhere in this description. It is to be understood that comparing as used herein usually refers to a comparison of corresponding parameters or values, e.g., an absolute amount is compared to an absolute reference level while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

The term "reference level" as used herein preferably refers to a predetermined value. In this context "level" encompasses the absolute amount, the relative amount or concentration as well as any value or parameter which correlates thereto or can be derived therefrom. As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. In one embodiment the reference level is determined in reference samples from healthy individuals. The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated. In one embodiment the reference level is set to the median value as determined from the overall distribution of the values in a disease entity investigated. The reference level may vary depending on various physiological parameters such as age, gender or subpopulation, as well as on the means used for the determination of the biomarker as referred to herein. In one embodiment, the reference sample is from essentially the same type of cells, tissue, organ or body fluid source as the sample from the individual or patient subjected to the method of the invention, e.g. if according to the invention blood is used as a sample to determine the level of the biomarker in the individual, the reference level is also determined in blood or a part thereof.

The term "reference level" as used herein, preferably, refers to an level which allows for allocation of a patient into either the group of patients which are more likely to respond to a therapy comprising a statin, or into a group of patients which are less likely to respond to a therapy comprising a statin. Such a reference level can be a threshold level which separates these groups from each other. Accordingly, the reference level for a biomarker as referred to herein, shall be a level which allows for allocation of a patient into a group of patients who is more likely to respond to a therapy comprising a statin, or who is less likely to respond to a therapy comprising a statin. A suitable threshold level separating the two groups can be calculated without further ado by the statistical tests referred to herein elsewhere based on the level of the marker as referred to herein from either a patient who is more likely to respond to a therapy comprising a statin (or from a group of such patients), or a patient who is less likely to respond to a therapy comprising a statin (or from a group of such patients). Preferred reference levels which can be derived from the aforementioned patients or group of patients are indicated elsewhere herein.

The reference level may be used to define and establish a threshold level. The threshold level, preferably, allows for identifying a patient as more likely or less likely to respond to a therapy comprising a statin. Thus, the reference level, preferably, shall allow for identifying a patient as more likely or less likely to respond to a therapy comprising a statin. In an embodiment, said reference level is a calculated reference level. The identification may be provided by the computing device of a system disclosed herein based on said comparison of the calculated "level" to a reference or a threshold. For example, a computing device of a system may provide an indicator, in the form of a word, symbol, or numerical value which is indicative of a rule-in or rule-out. The reference level applicable for an individual patient may vary depending on various physiological parameters such as age, gender, or subpopulation, as well as on the means used for the determination of the polypeptide or peptide referred to herein. A suitable reference level may be determined from a reference sample to be analyzed together, i.e. simultaneously or subsequently, with the test sample.

Preferably, the reference level is a calculated reference level. Preferably, the calculated reference level shall allow for differentiating between a patient who is more likely to respond to a therapy comprising a statin, and patient who is less likely to respond to a therapy comprising a statin. Reference levels can, in principle, be calculated for a cohort of patients as specified above based on the average or mean values for a given biomarker by applying standard statistically methods. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity/specificity pairs resulting from continuously varying the decision threshold over the entire range of data observed. The clinical performance of a diagnostic method depends on its accuracy, i.e. its ability to correctly allocate patients to a certain assessment, prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present invention can be, preferably, a threshold or cut off level and can be generated, preferably, by establishing a ROC for said cohort as described above and deriving a threshold level therefrom. Dependent on a desired sensitivity and specificity for a diagnostic method, the ROC plot allows deriving suitable thresholds.

The following applies as diagnostic algorithms:

Osteopontin as Biomarker

If Osteopontin is used as biomarker, the heart failure patient to be tested, preferably, does not suffer from coronary artery disease. Preferably, a level of the biomarker in the sample of the patient below the reference level indicates that the patient is more likely to respond to the therapy comprising a statin. Also preferably, a level of the biomarker above the reference level indicates that the patient is less likely to respond to the therapy comprising a statin.

sST2 as Biomarker

If sST2 is used as biomarker, the heart failure patient to be tested, preferably, does not suffer from coronary artery disease. Preferably, a level of the biomarker in the sample of the patient below the reference level indicates that the patient is more likely to respond to the therapy comprising a statin. Also preferably, a level of the biomarker in the sample from the patient above the reference level indicates that the patient is less likely to respond to the therapy comprising a statin.

GDF-15 as Biomarker

If GDF-15 is used as biomarker, the heart failure patient to be tested may or may not suffer from coronary artery disease.

If the patient does not suffer from coronary artery disease, the following applies: Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

If the patient suffers from coronary artery disease, the following applies: Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

Urea as Biomarker

If urea is used as biomarker, the heart failure patient to be tested may or may not suffer from coronary artery disease. However, it is in particular envisaged that the patient suffers from CAD. Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

Uric Acid as Biomarker

If uric acid is used as biomarker, the patient to be tested may or may not suffer from coronary artery disease. However, it is in particular envisaged that the patient suffers from CAD. Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

Transferrin as Biomarker

If Transferrin is used as biomarker, the patient to be tested, preferably, also suffers from coronary artery disease. Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

Cardiac Troponin as Biomarker

If a cardiac Troponin, in particular Troponin T, is used as biomarker, the patient to be tested may or may not additionally suffer from coronary artery disease.

If the patient does not suffer from coronary artery disease, the following applies: Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

If the patient suffers from coronary artery disease, the following applies: Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

SHBG as Biomarker

If SHBG, is used as biomarker, the patient to be tested may or may not suffer from coronary artery disease.

If the patient does not suffer from coronary artery disease, the following applies: Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

If the patient suffers from coronary artery disease, the following applies: Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

sFlt-1 as Biomarker

If sFlt-1 is used as biomarker, the patient to be tested may or may not suffer from coronary artery disease. However, it is in particular envisaged that the patient suffers from CAD. Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

Prealbumin as Biomarker

If Prealbumin is used as biomarker, the patient to be tested may or may not suffer from coronary artery disease.

If the patient does not suffer from coronary artery disease, the following applies: Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

If the patient suffers from coronary artery disease, the following applies: Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

PlGF as Biomarker

If PlGF is used as biomarker, the patient to be tested may or may not suffer from coronary artery disease. However, it is in particular envisaged that the patient suffers from CAD. Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

IL-6 as Biomarker

If IL-6 is used as biomarker, the patient to be tested may or may not suffer from coronary artery disease. However, it is in particular envisaged that the patient suffers from CAD. Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

Ferritin as Biomarker

If Ferritin is used as biomarker, the patient to be tested, preferably also suffers from coronary artery disease. Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

hsCRP as Biomarker

If hsCRP is used as biomarker, the patient to be tested may or may not suffer from coronary artery disease.

If the patient does not suffer from coronary artery disease, the following applies: Preferably, a level of the biomarker in the sample from the patient above the reference level indicates that the patient is more likely to respond to the therapy comprising a statin. Also preferably, a level of the biomarker in the sample from the patient below the reference level indicates that the patient is less likely to respond to the therapy comprising a statin.

If the patient suffers from coronary artery disease, the following applies: Preferably, a level of the biomarker in the sample from the patient below the reference level indicates that the patient is more likely to respond to the therapy comprising a statin. Also preferably, a level of the biomarker in the sample from the patient above the reference level indicates that the patient is less likely to respond to the therapy comprising a statin.

As set forth above, reference levels can be determined without further ado. A preferred referenced levels may the Median level of a group of patients having heart failure.

Preferred diagnostic algorithms for the individual markers are also disclosed in the section "Preferred embodiments", see e.g. embodiment 8.

A preferred reference level for GDF-15 is preferably within the range of between 2500 pg/mL and 4500 pg/mL, more preferably, within the range of between 3000 pg/mL and 4000 pg/mL. Most preferably, the reference level is 3560 pg/mL.

A preferred reference level for Urea is preferably within the range of between 8 mmol/L and 11 mmol/L, more preferably, within the range of between 9 mmol/L and 10 mmol/L. Most preferably, the reference level is 9.4 mmol/L.

A preferred reference level for SHBG is preferably within the range of between 25 nmol/L and 36 nmol/L, more preferably, within the range of between 30 nmol/L and 32 nnmol/L. Most preferably, the reference level is 30.8 nmol/L.

A preferred reference level for Uric acid is preferably within the range of between 6.3 mg/dL and 8.3 mg/dL, more preferably, within the range of between 6.9 mg/dL and 7.7 mg/dL. Most preferably, the reference level is 7.3 mg/dL.

A preferred reference level for PLGF is preferably within the range of between 16 pg/mL and 26 pg/mL, more preferably, within the range of between 20 pg/mL and 23 pg/mL. Most preferably, the reference level is 21.3 pg/mL.

A preferred reference level for IL-6 is preferably within the range of between 5.7 pg/mL and 7.1 pg/mL, more preferably, within the range of between 6.1 pg/mL and 6.7 pg/mL. Most preferably, the reference level is 6.4 pg/mL.

A preferred reference level for Transferrin is preferably within the range of between 3.7 g/L and 4.5 g/L, more preferably, within the range of between 3.9 g/L and 4.3 g/L. Most preferably, the reference level is 4.1 g/L.

A preferred reference level for Troponin is preferably within the range of between 20 pg/mL and 31 pg/mL, more preferably, within the range of between 25 pg/mL and 28 pg/mL. Most preferably, the reference level is 26.5 pg/mL.

A preferred reference level for sFlt-1 is preferably within the range of between 85 pg/mL and 115 pg/mL, more preferably, within the range of between 93 pg/mL and 107 pg/mL. Most preferably, the reference level is 99.6 pg/mL.

A preferred reference level for Prealbumin is preferably within the range of between 0.18 g/L and 0.22 g/L, more preferably, within the range of between 0.19 g/L and 0.21 g/L. Most preferably, the reference level is 0.2 g/L.

A preferred reference level for Ferritin is preferably within the range of between 140 µg/L between and 180 µg/L, more preferably, within the range of between 150 µg/L and 170 µg/L. Most preferably, the reference level is 160 µg/L.

A preferred reference level for Osteopontin is preferably within the range of between 85 ng/mL and 115 ng/mL, more preferably, within the range of between 93 ng/mL and 107 ng/mL. Most preferably, the reference level is 100 ng/mL.

A preferred reference level for sST2 is preferably within the range of between 30 ng/mL and 38 ng/mL, more preferably, within the range of between 32 ng/mL and 36 ng/mL. Most preferably, the reference level is 34 ng/mL.

A preferred reference level for hsCRP is preferably within the range of between 4 mg/mL and 6 mg/mL, more preferably, within the range of between 4.8 mg/mL and 5.4 mg/mL. Most preferably, the reference level is 5.1 mg/mL.

The referenced levels given above, preferably, apply to all methods and uses of the present invention.

In certain embodiments, the term "above the reference level" refers to a level of the biomarker in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in biomarker level in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

In certain embodiments, the term "decrease" or "below" herein refers to a level of the biomarker in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease in biomarker level in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

In an embodiment of the invention, the biomarkers are measured alone. However, it is also contemplated to may be determined together, i.e. the method of the present invention may encompass the determination of more than one marker, i.e. of two, three, four or five markers. If more than one marker is determined, the diagnostic algorithms for the individual markers are combined.

Preferred biomarker combinations are as follows:
GDF-15 and Urea
GDF-15 and SHBG
GDF-15 and PlGF
GDF-15 and IL-6
PlGF and IL-6
Troponin and sST2
hsCRP and sST2
PLGF and sFlt1

In an embodiment of the method of the present invention, the aforementioned method further comprises step (d) of recommending, initiation or discontinuing a therapy comprising a statin.

The phrase "recommending a therapy" as used herein refers to using the information or data generated relating to the level of the at least one biomarker as referred to herein in a sample of a patient to identify the patient as suitably treated or not suitably treated with a therapy comprising a statin. The phrase "recommending a therapy" as used herein also may refer to using the information or data generated for proposing or selecting a therapy comprising a statin for a patient identified or selected as more or less likely to respond to the therapy comprising a statin. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of at least one biomarker as referred to herein to a reference level.

Preferably, if the patient is more likely to respond to a therapy comprising a statin, a therapy comprising a statin is initiated (in case the patient was not previously treated with a statin), or continued (in case the patient was not previously treated with a statin). Thus, it is recommended to initiate or to continue a therapy comprising a statin.

Preferably, if the patient is less likely to respond to a therapy comprising a statin, a therapy comprising a statin is not initiated (in case the patient was not previously treated with a statin), or discontinued (in case the patient was not previously treated with a statin). Thus, it is recommended not to initiate or to discontinue a therapy comprising a statin.

Accordingly, the present invention also pertains to a method of treating a patient having heart failure, the method comprising
 a) measuring of the level at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from the patient,
 b) comparing the level said at least one biomarker measured in a) to a respective reference level,
 c) identifying the patient as more likely or less likely to respond to the therapy comprising a statin, and optionally
 d) administering a statin to the patient or selecting the therapy comprising a statin when the level of the at least one biomarker is indicative for a therapy comprising a statin.

By step d) of the aforementioned therapy heart failure is treated.

In an embodiment, the identification of a patient as more likely or less likely to respond to the therapy comprising a statin as set forth in step c), is based on the comparison carried out in step b). Preferred diagnostic algorithms for the individual markers are disclosed elsewhere herein. Depending on the biomarker, a level of the biomarker in the sample from the patient of either above or below the reference level is indicative for a patient who is more likely to respond to a therapy comprising a statin (see diagnostic algorithms set forth above). If the level of the biomarker is indicative for a patient who is more likely to respond to a therapy comprising a statin, step d) is carried out. If the level of the biomarker is indicative for a patient who is less likely to respond to a therapy comprising a statin, step d) is not carried out.

The definitions and explanations given herein above apply mutatis mutandis to the following (except if stated otherwise).

Method of Predicting the Risk of a Patient of Mortality and/or Hospitalization

The present invention is further directed to a method of predicting the risk of a patient of mortality and/or hospitalization, wherein said patient has heart failure and wherein said patient is undergoing a therapy comprising a statin, said method comprising:
 (a) measuring a level of at least one marker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from a patient, and
 (b) comparing the level of the at least one marker to a respective reference level.

The method of the present invention, preferably, is an ex vivo or in vitro method.

Preferably, the risk of the patient to suffer from death or hospitalization is predicted, based on step (b). According, the aforementioned method may further comprise the step of predicting the risk of a patient to suffer from death or hospitalization based on the results of step (b). In an embodiment, the method thus further comprises step (c) of predicting the risk of mortality and/or hospitalization of the patient, in particular when the level of the at least one biomarker in the sample from the patient is below or above the reference level (for diagnostic algorithms, see below).

In an embodiment, the level of the at least one biomarker is measured by contacting the sample with an agent that specifically binds to the respective marker, thereby forming a complex between the agent and said marker, detecting the amount of complex formed, and thereby measuring the level of said marker. This applies in particular, if the biomarker to be measured is a polypeptide (GDF-15, SHBG, PLGF IL-6 Transferrin, a cardiac Troponin, sFlt-1, Prealbumin, Ferritin, Osteopontin, sST2, and hsCRP). If the biomarker to be measured is urea or uric acid, the level of said biomarker is measured by contacting the sample with enzyme that catalyzes the conversion of said biomarker. Preferred enzymes are disclosed elsewhere herein.

The term "patient" has been defined above in the context of the method of identifying a subject as likely to respond to a therapy comprising a statin. Preferably, the patient to be tested has heart failure as set forth above. Depending on the biomarker to be measured, the patient additionally may have coronary artery disease, or not (see above).

Moreover, the patient shall undergo a therapy comprising a statin. Accordingly, the patient shall have been treated with a statin prior to obtaining the sample. In the context of the present invention, a patient who has been treated with a statin prior to obtaining the sample shall have been treated with a statin preferably for one month or more, more preferably for three months or more, or most preferably, for six months or more prior to obtaining the sample.

The term "predicting" used herein refers to assessing the probability according to which a patient will die and/or will be hospitalized within a defined time window (predictive window) in the future. The predictive window is an interval in which the patient will die or will be hospitalized according to the predicted probability. The predictive window may be the entire remaining lifespan of the patient upon analysis by the method of the present invention. Preferably, however, the predictive window is an interval of 6 months, 12 months, 18 months, two years, three years, or five years after the method of the present invention has been carried out (more preferably and precisely, after the sample to be analyzed by the method of the present invention has been obtained). Most preferably, said predictive window is an interval of 18 months. As will be understood by those skilled in the art, such an assessment is usually not intended to be correct for 100% of the patients to be analyzed. The term, however, requires that the assessment will be valid for a statistically significant portion of the patients to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the patients of a given cohort.

The term "mortality" as used herein, preferably, relates to mortality from any cause, and, more preferably, from cardiac causes, and most preferably, from a cardiovascular event. Also, the term "hospitalization" as used herein, preferably, relates to hospitalization from any cause, and, more preferably, from cardiac causes, and most preferably, from a cardiovascular event. The term "cardiovascular event" as used herein refers to any disorder of the cardiovascular system including preferably any acute cardiovascular event. Preferably, the term also includes heart failure. Acute cardiovascular events are, preferably, stable angina pectoris (SAP) or acute coronary syndrome (ACS). ACS patients can show unstable angina pectoris (UAP) or myocardial infarction (MI). MI can be an ST-elevation MI (STEMI) or a non-ST-elevation MI (NSTEMI). NSTE-ACS as used herein encompasses UAP and NSTEMI. The occurring of an MI can be followed by a left ventricular dysfunction (LVD), development of heart failure or even mortality. Further preferred cardiovascular events encompass cardiac brady- or tachyarrhythmias including sudden cardiac death and stroke (cerebrovascular events or accidents). Also, mortality can also refer to the death rate or the ratio of number of deaths to a given population of patients.

The expression "predicting the risk of mortality and/or hospitalization" as used herein means that it the patient to be analyzed by the method of the present invention is allocated either into the group of patients of a population having an elevated risk, or into a group having a reduced risk. An elevated risk as referred to in accordance with the present invention, preferably, means that the risk of hospitalization or the risk of mortality within a predetermined predictive window is elevated significantly (i.e. increased significantly) for a patient with respect to the average risk of hospitalization or mortality in a population of patients. A reduced risk as referred to in accordance with the present invention, preferably, means that the risk of hospitalization or the risk of mortality within a predetermined predictive window is reduced significantly for a patient with respect to the average risk of hospitalization or mortality in a population of patients. Particularly, a significant increase or reduction of a risk is an increase or reduction or a risk of a size which is considered to be significant for prognosis, particularly said increase or reduction is considered statistically significant. The terms "significant" and "statistically significant" are known by the person skilled in the art. Thus, whether an increase or reduction of a risk is significant or statistically significant can be determined without further ado by the person skilled in the art using various well known statistic evaluation tools.

Preferably, for a predictive window of 18 months, an elevated, and, thus increased risk of mortality and/or hospitalization as used herein, preferably, relates to a risk increase of more than 20%, or, more preferably, of more than 25%, and most preferably, of more than 30%. A reduced risk of mortality or of hospitalization as used herein, preferably, relates to a risk reduction of more than 10% more preferably, of more than 15%, and, most preferably, of more than 20%, preferably with respect to a predictive window of 18 months (as compared to the average risk, see last paragraph).

The term "reference level" has been defined above. The definition applies accordingly. Thus, the term, preferably, refers to a level which allows for allocation of a patient into either the group of patients who has an elevated risk of mortality and/or of hospitalization, or into a group of patients who has a reduced risk of mortality and/or of hospitalization. Such a reference level can be a threshold level which separates these groups from each other. Accordingly, the reference level for a biomarker as referred to herein, shall be a level which allows for allocation of a patient into a group of patients who has an elevated risk of mortality and/or of hospitalization, or who has a reduced risk of mortality and/or of hospitalization. A suitable threshold level separating the two groups can be calculated without further ado by the statistical tests referred to herein elsewhere based on the level of the marker as referred to herein from either a patient who has an elevated risk of mortality and/or of hospitalization (or from a group of such patients), or a patient who has a reduced risk of mortality and/or of hospitalization (or from a group of such patients). Preferred reference levels which can be derived from the aforementioned patients or group of patients are indicated elsewhere herein.

Osteopontin as Biomarker

If Osteopontin is used as biomarker, the patient to be tested, preferably, does not suffer from coronary artery disease. Preferably, a level of the biomarker in the sample of the patient above the reference level indicates that the patient has an elevated risk of mortality and/or hospitalization. Also preferably, a level of the biomarker below the reference level indicates that the patient has a reduced risk of mortality and/or hospitalization.

sST2 as Biomarker

If sST2 is used as biomarker, the patient to be tested, preferably, does not suffer from coronary artery disease. Preferably, a level of the biomarker in the sample of the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

GDF-15 as Biomarker

If GDF-15 is used as biomarker, the patient to be tested may or may not suffer from coronary artery disease.

If the patient does not suffer from coronary artery disease, the following applies: Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

If the patient suffers from coronary artery disease, the following applies: Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

Urea as Biomarker

If urea is used as biomarker, the patient to be tested may or may not suffer from coronary artery disease. However, it is in particular envisaged that the patient suffers from CAD. Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

Uric Acid as Biomarker

If uric acid is used as biomarker, the patient to be tested may or may not suffer from coronary artery disease. However, it is in particular envisaged that the patient suffers from CAD. Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

Transferrin as Biomarker

If Transferrin is used as biomarker, the patient to be tested, preferably, also suffers from coronary artery disease. Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

Cardiac Troponin as Biomarker

If a cardiac Troponin, in particular Troponin T, is used as biomarker, the patient to be tested may or may not additionally suffer from coronary artery disease.

If the patient does not suffer from coronary artery disease, the following applies: Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

If the patient suffers from coronary artery disease, the following applies: Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

SHBG as Biomarker

If SHBG, is used as biomarker, the patient to be tested may or may not suffer from coronary artery disease.

If the patient does not suffer from coronary artery disease, the following applies: Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

If the patient suffers from coronary artery disease, the following applies: Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

sFlt-1 as Biomarker

If sFlt-1 is used as biomarker, the patient to be tested may or may not suffer from coronary artery disease. However, it is in particular envisaged that the patient suffers from CAD. Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

Prealbumin as Biomarker

If Prealbumin is used as biomarker, the patient to be tested may or may not suffer from coronary artery disease.

If the patient does not suffer from coronary artery disease, the following applies: Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization If the patient suffers from coronary artery disease, the following applies: Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

PlGF as Biomarker

If PlGF is used as biomarker, the patient to be tested may or may not suffer from coronary artery disease. However, it is in particular envisaged that the patient suffers from CAD. Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

IL-6 as Biomarker

If IL-6 is used as biomarker, the patient to be tested may or may not suffer from coronary artery disease. However, it is in particular envisaged that the patient suffers from CAD. Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

Ferritin as Biomarker

If Ferritin is used as biomarker, the patient to be tested, preferably also suffers from coronary artery disease. Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

hsCRP as Biomarker

If hsCRP is used as biomarker, the patient to be tested may or may not suffer from coronary artery disease.

If the patient does not suffer from coronary artery disease, the following applies: Preferably, a level of the biomarker in the sample from the patient below the reference level indicates that the patient has an elevated risk of mortality and/or hospitalization. Also preferably, a level of the biomarker in the sample from the patient above the reference level indicates that the patient has a reduced risk of mortality and/or hospitalization.

If the patient suffers from coronary artery disease, the following applies: Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization.

Preferred reference levels are disclosed in the context of the method of identifying a patient as susceptible to a therapy comprising a statin. Preferred diagnostic algorithms for the individual markers are also disclosed in the section "Preferred embodiments", see e.g. embodiment 10. The present invention also relates to the use of i) at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) and/or ii) of a binding agent which specifically binds to a biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), or iii) of an enzyme or of compound that allows for the conversion of uric acid or urea, in a sample of a patient having heart failure for identifying a patient as likely to respond to a therapy comprising a statin.

The present invention also relates to the use of i) at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) and/or of ii) a binding agent which specifically binds to a biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), or iii) of an enzyme or of compound that allows for the conversion of uric acid or urea in a sample of a patient having heart failure for predicting the risk of mortality and/or of hospitalization of said patient.

The present invention also relates to the use of i) at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) and/or of ii) of a binding agent which specifically binds to a biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), or iii) of an enzyme or of compound that allows for the conversion of uric acid or urea for the manufacture of a pharmaceutical or diagnostic composition for identifying a patient having heart failure as likely to respond to a therapy comprising a statin.

The present invention also relates to the use of i) at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) and/or of ii) of a binding agent which specifically binds to a biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), or iii) of an enzyme or of compound that allows for the conversion of uric acid or urea for the manufacture of a pharmaceutical or diagnostic composition for predicting the risk of mortality and/or of hospitalization a patient who has heart failure and who undergoes a therapy comprising a statin.

According to a preferred embodiment of the present invention, a device adapted for carrying out a method of the invention is provided comprising a) an analyzer unit comprising at least one binding agent which specifically binds to at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin (Soluble fms-like tyrosine kinase-1), Prealbumin, Ferritin, Osteopontin, sST2 (soluble ST2), and hsCRP (high sensitivity C-reactive protein), or of an enzyme or of compound that allows for the conversion of uric acid or urea said unit being adapted for measuring the level(s) of the biomarker(s) in a sample of a patient having heart failure, and b) an analyzer unit for comparing the determined level(s) with reference level(s), whereby a patient is identified as more or less likely to respond to a therapy comprising a statin, said unit comprising a database with a reference level (or levels) and a computer-implemented algorithm for carrying out the comparison.

According to another preferred embodiment of the present invention, a device adapted for carrying out a method of the invention is provided comprising a) an analyzer unit comprising an binding agent (or binding agents) which specifically binds to at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), or iii) of an enzyme or of compound that allows for the conversion of uric acid or urea, said unit being adapted for measuring the level(s) of the biomarker(s) in a sample of a patient having heart failure, and b) an analyzer unit for comparing the determined level(s) with reference level(s), whereby the risk of a patient of mortality and/or hospitalization is predicted, said unit comprising a database with a reference level (or levels) and a computer-implemented algorithm for carrying out the comparison.

Preferred reference levels and algorithms are disclosed elsewhere herein.

A preferred embodiment of the instant disclosure includes a system for identifying a patient as likely to respond to a therapy comprising a statin. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable prepreamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the level of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined level of one or more markers disclosed herein, and a suitable reference, is embodied and performed by executing the instructions. The results may be given as output of parametric diagnostic raw data or as absolute or relative levels. According to various embodiments of the system disclosed herein, a "diagnosis" may be provided by the computing device of a system disclosed herein based on said comparison of the calculated "level" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

Finally, the invention pertains to a kit adapted for carrying out a method of the present invention comprising at least one binding agent which specifically binds to at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) reference standards as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above, i.e. a solution with a pre-defined level for the biomarker as referred to herein representing a reference level.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilized in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in separate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), provided in a single container. In some such embodiments, an immobilized probe may be provided in multiple different containers (e.g., in single-use form), or multiple immobilized probes may be provided in multiple different containers. In further embodiments, the probes may be immobilized on multiple different type of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, he kits may comprise a single container or multiple containers, and where multiple containers are present, each container may be the same as all other containers, different than others, or different than some but not all other containers.

In addition, the present invention is directed to a statin for use for treating heart failure in a patient having a level (preferably in a sample, more preferably in a blood, serum or plasma sample, most preferably, in a plasma sample) of at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) which is above or below a respective reference level.

Finally, the present invention pertains to the use of a statin for the manufacture of a medicament for the treatment of heart failure in a patient having (preferably in a sample, more preferably in a blood, serum or plasma sample, most preferably, in a plasma sample) a level of at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) which is above or below a respective reference level (for the respective marker).

In an embodiment, the level is the blood, serum or plasma level, in particular the plasma level.

Moreover, as set forth herein above, the patient may additionally suffer from coronary artery disease, or may not suffer from coronary artery disease.

Preferred reference levels are disclosed elsewhere herein.

Osteopontin as Biomarker

If the biomarker is Osteopontin, the patient preferably, does not suffer from coronary artery disease. Preferably, the patient to be treated has a level of the biomarker below the reference level for this biomarker.

sST2 as Biomarker

If the biomarker is sST2, the patient, preferably, does not suffer from coronary artery disease. Preferably, the patient to be treated has a level of the biomarker below the reference level for this biomarker.

GDF-15 as Biomarker

If the biomarker is GDF-15, the patient may or may not suffer from coronary artery disease.

If the patient does not suffer from coronary artery disease, the following applies: Preferably, the patient to be treated has a level of the biomarker above the reference level for this biomarker.

If the patient suffers from coronary artery disease, the following applies: Preferably, the patient to be treated has a level of the biomarker below the reference level for this biomarker.

Urea as Biomarker

If the biomarker is urea, the patient may or may not suffer from coronary artery disease. However, it is in particular envisaged that the patient suffers from CAD. Preferably, the patient to be treated has a level of the biomarker above the reference level for this biomarker.

Uric Acid as Biomarker

If the biomarker is uric acid, the patient may or may not suffer from coronary artery disease. However, it is in particular envisaged that the patient suffers from CAD. Preferably, the patient to be treated has a level of the biomarker below the reference level for this biomarker.

Transferrin as Biomarker

If the biomarker is Transferrin, the patient preferably, also suffers from coronary artery disease. Preferably, the patient to be treated has a level of the biomarker above the reference level for this biomarker.

Cardiac Troponin as Biomarker

If the biomarker is a cardiac Troponin, in particular Troponin T, the patient may or may not additionally suffer from coronary artery disease.

If the patient does not suffer from coronary artery disease, the following applies: Preferably, the patient to be treated has a level of the biomarker below the reference level for this biomarker.

If the patient suffers from coronary artery disease, the following applies: Preferably, the patient to be treated has a level of the biomarker above the reference level for this biomarker.

SHBG as Biomarker

If the biomarker is SHBG, the patient may or may not suffer from coronary artery disease.

If the patient does not suffer from coronary artery disease, the following applies: Preferably, the patient to be treated has a level of the biomarker below the reference level for this biomarker.

If the patient suffers from coronary artery disease, the following applies: Preferably, the patient to be treated has a level of the biomarker above the reference level for this biomarker.

sFlt-1 as Biomarker

If the biomarker is sFlt-1, the patient may or may not suffer from coronary artery disease. However, it is in particular envisaged that the patient suffers from CAD. Preferably, the patient to be treated has a level of the biomarker below the reference level for this biomarker.

Prealbumin as Biomarker

If the biomarker is Prealbumin, the patient may or may not suffer from coronary artery disease.

If the patient does not suffer from coronary artery disease, the following applies: Preferably, the patient to be treated has a level of the biomarker above the reference level for this biomarker.

If the patient suffers from coronary artery disease, the following applies: Preferably, the patient to be treated has a level of the biomarker below the reference level for this biomarker.

PlGF as Biomarker

If the biomarker is PlGF, the patient may or may not suffer from coronary artery disease. However, it is in particular envisaged that the patient suffers from CAD. Preferably, a level of the biomarker in the sample from the patient above the reference level indicates that the patient has an elevated risk of mortality and/or hospitalization. Also preferably, a level of the biomarker in the sample from the patient below the reference level indicates that the patient has a reduced risk of mortality and/or hospitalization IL-6 as Biomarker If the biomarker is IL-6, the patient may or may not suffer from coronary artery disease. However, it is in particular envisaged that the patient suffers from CAD. Preferably, the patient to be treated has a level of the biomarker above the reference level for this biomarker.

Ferritin as Biomarker

If the biomarker is Ferritin, the patient preferably also suffers from coronary artery disease. Preferably, the patient to be treated has a level of the biomarker below the reference level for this biomarker.

hsCRP as Biomarker

If the biomarker is hsCRP, the patient may or may not suffer from coronary artery disease.

If the patient does not suffer from coronary artery disease, the following applies: Preferably, the patient to be treated has a level of the biomarker above the reference level for this biomarker.

If patient suffers from coronary artery disease, the following applies: Preferably, the patient to be treated has a level of the biomarker below the reference level for this biomarker.

Preferred reference levels are indicated herein above in connection with the method of identifying a patient as likely to respond to a therapy comprising a statin. Preferred diagnostic algorithms for the individual markers are also disclosed in following section "Preferred embodiments", see embodiment 16.

PREFERRED EMBODIMENTS

In the following, preferred embodiments of the present invention are disclosed. The definitions given above apply mutatis mutandis.

1. A method of identifying a patient having heart failure as likely to respond to a therapy comprising a statin comprising:
   (a) measuring a level of at least one biomarker selected from GDF-15 (Growth Differentiation Factor 15), SHBG (Sex Hormone-Binding Globulin), PLGF (Placental Growth Factor), IL-6 (Interleukin-6), Urea, Uric acid, Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from the patient, and
   (b) comparing the level of the at least one marker to a respective reference level.
2. The method according to embodiment 1, wherein the subject has heart failure classified as stage B, C or D according to the ACC/AHA classification, in particular heart failure classified as stage B or C, and/or heart failure classified as NYHA class II, III, IV, in particular heart failure classified are classified as NYHA class II or III according to the NYHA classification.

3. The method of embodiments 1 and 2, wherein the patient also has coronary artery disease, in particular wherein the at least one biomarker is transferrin, ferritin, urea, uric acid, sFlt-1, PlGF or IL-6.
4. The method of embodiments 1 and 2, wherein the patient does not have coronary artery disease, in particular wherein the biomarker is osteopontin or sST2.
5. The method of any one of embodiments 1 to 4, wherein the statin is selected from the group consisting of from the group consisting of Atorvastatin, Cerivastatin, Fluvastatin, Lovastatin, Mevastatin, Pitavastatin, Pravastatin, Rosuvastatin and Simvastatin.
6. The method of any one of embodiments 1 to 5, wherein the patient has been treated with a statin prior to obtaining the sample.
7. The method of any one of embodiments 1 to 6, wherein the patient has not been treated with a statin prior to obtaining the sample.
8. The method of any one of embodiments 1 to 7, wherein
   i) the at least one biomarker is GDF-15, and
      a) wherein the patient does not suffer from coronary artery disease, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin, or
      b) wherein the patient suffers from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin,
   ii) the at least one biomarker is SHBG, and
      a) wherein the patient does not suffer from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin, or
      b) wherein the patient suffers from coronary artery disease, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin,
   iii) the at least one biomarker is PlGF, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin,
   iv) the at least one biomarker is IL-6, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin,
   v) the at least one biomarker is urea, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin,
   vi) the at least one biomarker is osteopontin, and wherein the patient does not suffer from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin,
   vii) the at least one biomarker is sST2, and wherein the patient does not suffer from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin,
   viii) the at least one biomarker is uric acid, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin,
   ix) the at least one biomarker is sFlt-1, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin,
   x) the at least one biomarker is transferrin, and wherein the patient also suffers from coronary artery disease, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin,
   xi) the at least one biomarker is ferritin, and wherein the patient also suffers from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin, xii) the at least one biomarker is a cardiac Troponin, and
  a) wherein the patient does not suffer from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin, or
  b) wherein the patient suffers from coronary artery disease, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin, and/or
xiii) wherein the at least one biomarker is Prealbumin and/or hsCRP, and
  a) wherein the patient does not suffer from coronary artery disease, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin, or
  b) wherein the patient suffers from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin.

9. A method of predicting the risk of a patient of mortality and/or hospitalization, wherein said patient has heart failure and wherein said patient is undergoing a therapy comprising a statin, said method comprising:
  (a) measuring a level of at least one marker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) in a sample from said patient, and
  (b) comparing the level of the at least one marker to a respective reference level.

10. The method according to embodiment 9, wherein
  i) the at least one biomarker is GDF-15, and
    a) wherein the patient does not suffer from coronary artery disease, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization, or
    b) wherein the patient suffers from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization,
  ii) the at least one biomarker is SHBG, and
    a) wherein the patient does not suffer from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization, or
    b) wherein the patient suffers from coronary artery disease, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization,
  iii) the at least one biomarker is PlGF, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization,
  iv) the at least one biomarker is IL-6, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization,
  v) the at least one biomarker is urea, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization,
  vi) the at least one biomarker is osteopontin, and wherein the patient does not suffer from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization,
  vii) the at least one biomarker is sST2, and wherein the patient does not suffer from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization, viii) the at least one biomarker is uric acid, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization, ix) the at least one biomarker is sFlt-1, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization, x) the at least one biomarker is transferrin, and wherein the patient also suffers from coronary artery disease, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization, xi) the at least one biomarker is ferritin, and wherein the patient also suffers from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization, xii) the at least one biomarker is a cardiac Troponin, and
  a) wherein the patient does not suffer from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization, or
  b) wherein the patient suffers from coronary artery disease, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization, and/or xiii) the at least one biomarker is Prealbumin and/or hsCRP, and
  a) wherein the patient does not suffer from coronary artery disease, and wherein a level of the biomarker in the sample from the patient above the reference level indicates that the patient has a reduced risk of mortality and/or hospitalization, and/or wherein a level of the biomarker in the sample from the patient below the reference level indicates that the patient has an increased risk of mortality and/or hospitalization, or
  b) wherein the patient suffers from coronary artery disease, and wherein a level of the biomarker in the sample from the patient below the reference level indicates that the patient has a reduced risk of mortality and/or hospitalization, and/or wherein a level of the biomarker in the sample from the patient above the reference level indicates that the patient has an increased risk of mortality and/or hospitalization.

11. The method according to any one of embodiments 1 to 10, wherein the sample is a blood, serum or plasma sample.

12. The method according to any one of embodiments 1 to 11, wherein the patient is a human.

13. Use of i) at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) and/or of ii) of at least one binding agent which specifically binds to a biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), in a sample of a patient having heart failure for identifying a patient as likely to respond to a therapy comprising a statin.

14. Use of i) at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) and/or of ii) of at least one binding agent which specifically binds to a biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), in a sample of a patient having heart failure for predicting the risk of mortality and/or of hospitalization of said patient.

15. A device for carrying out the method according to any one of embodiments 1 to 8, said device comprising
  a) an analyzer unit comprising at least one binding agent which specifically binds to at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein), said unit being adapted for measuring the level(s) of the biomarker(s) in a sample of a patient having heart failure, and
  b) an analyzer unit for comparing the determined level(s) with reference level(s), whereby a patient is identified as more or less likely to respond to a therapy comprising a statin, said unit comprising a database with a reference level (or levels) and a computer-implemented diagnostic algorithm for carrying out the comparison, in particular, wherein the diagnostic algorithm is a algorithm as set forth in claim 8.

16. A statin for use for treating heart failure in a patient having a level, in particular a blood, serum or plasma level, of at least one biomarker selected from GDF-15 (Growth Differentiation Factor 15), Urea, SHBG (Sex Hormone-Binding Globulin), Uric acid, PLGF (Placental Growth Factor), IL-6 (Interleukin-6), Transferrin, a cardiac Troponin, sFlt-1 (Soluble fms-like tyrosine kinase-1), Prealbumin, Ferritin, Osteopontin, sST2 (soluble ST2), and hsCRP (high sensitivity C-reactive protein) which is above or below a respective reference level, in particular wherein
  i) the at least one biomarker is GDF-15, and
    a) wherein the patient does not suffer from coronary artery disease, and wherein the level of the biomarker is above the reference level, or
    b) wherein the patient suffers from coronary artery disease, and wherein the level of the biomarker is below the reference level,
  ii) the at least one biomarker is SHBG, and
    a) wherein the patient does not suffer from coronary artery disease, and wherein the level of the biomarker is below the reference level, or
    b) wherein the patient suffers from coronary artery disease, and wherein the level of the biomarker is above the reference level,
  iii) the at least one biomarker is PlGF, and wherein the level of the biomarker is above the reference level,
  iv) the at least one biomarker is IL-6, and wherein the level of the biomarker is above the reference level,
  v) the at least one biomarker is urea, and wherein the level of the biomarker is above the reference,
  vi) the at least one biomarker is osteopontin, and wherein the patient does not suffer from coronary artery disease, and wherein the level of the biomarker is below the reference level,
  vii) the at least one biomarker is sST2, and wherein the patient does not suffer from coronary artery disease, and wherein the level of the biomarker is below the reference level,
  viii) the at least one biomarker is uric acid, and wherein the level of the biomarker is below the reference level,
  ix) the at least one biomarker is sFlt-1, and wherein the level of the biomarker is below the reference level,
  x) the at least one biomarker is transferrin, and wherein the patient also suffers from coronary artery disease, and wherein the level of the biomarker is above the reference level,
  xi) the at least one biomarker is ferritin, and wherein the patient also suffers from coronary artery disease, and wherein the level of the biomarker is below the reference level,
  xii) the at least one biomarker is a cardiac Troponin, and
    a) wherein the patient does not suffer from coronary artery disease, and wherein the level of the biomarker is below the reference level, or
    b) wherein the patient suffers from coronary artery disease, and wherein the level of the biomarker is above the reference level, and/or
  xiii) the at least one biomarker is Prealbumin and/or hsCRP, and
    a) wherein the patient does not suffer from coronary artery disease, and wherein the level of the biomarker is above the reference level, or
    b) wherein the patient suffers from coronary artery disease, and wherein the level of the biomarker is below the reference level.

All references cited in this specification are herewith incorporated by reference with respect to their entire disclosure content and the disclosure content specifically mentioned in this specification.

EXAMPLES

The following Examples shall merely illustrate the invention. They shall not be construed, whatsoever, to limit the scope of the invention.

Example 1: Patient Cohort

Potential biomarker candidates for statin therapy stratification were measured in plasma samples from 499 patients suffering from HF (NYHA class II-IV HF (LVEF ≤45%) (Pfisterer M. et al. JAMA. 2009; 301:383-92). The biomarkers were measured at baseline and the subgroups below and above the median were associated with outcomes after 18 months of therapy. Additionally, patients were stratified for the presence of statin therapy and CAD (see Figures). 211 patients were not on statin therapy and 288 patients received statin therapy. Furthermore, 212 patients did not have Coronary Artery Disease (CAD) and 287 had CAD.

Example 2: Assays

Troponin T was determined using Roche's electrochemiluminescence ELISA sandwich test ELECSYS™ Troponin T hs (high sensitive) STAT (Short Turn Around Time) assay. The test employs two monoclonal antibodies specifically directed against human cardiac troponin T. The antibodies recognize two epitopes (amino acid position 125-131 and 136-147) located in the central part of the cardiac troponin T protein, which consists of 288 amino acids. The hs-TnT assay allows a measurement of troponin T levels in the range of 3 to 10000 pg/mL.

IL-6 (Interleukin 6) was measured by an electrochemiluminescent immunoassay (ECLIA, Roche Diagnostics). The test was performed using a COBAS® E601 analyzer from Roche Diagnostics. The test is based on a first incubation with a biotinylated monoclonal IL-6-specific antibody and a second incubation with a monoclonal IL-6-specific antibody labeled with a ruthenium complex and streptavidin-coated microparticles.

High-sensitive (hs) CRP was determined using a particle enhance immunoturbidimetric assay from Roche Diagnostics (Tina-quant Cardiac C-reactive Protein (Latex) High Sensitive). In this test, Anti-CRP antibodies coupled to latex microparticles react with antigen in the sample to form an antigen/antibody complex. Following agglutination, the complex is measured turbidimetrically.

sST2 was determined by using the Presage™ ST2 Assay from Critical Diagnostics (San Diego, Calif., USA). The assay is a quantitative sandwich monoclonal ELISA in a 96 well plate format for measurement of ST2 in serum or plasma. Diluted plasma was loaded into appropriate wells in the anti-ST2 antibody coated plate and incubated for the prescribed time. Following a series of steps where reagents are washed from the plate, and additional reagents were added and subsequently washed out, the analyte was finally detected by addition of a colorimetric reagent and the resulting signal was measured spectroscopically at 450 nm.

Prealbumin was measured in plasma samples by using the Roche COBAS® c system. The applied assay is an immunoturbidimetric assay. Human prealbumin forms a precipitate with a specific antiserum which is determined turbidimetrically.

PlGF and sFlt1 were tested using an ELECSYS™ immunoassay which employs two antibodies that are specific for PlGF and sFlt1, respectively. The test can be carried out automatically using different Roche analysers including ELECSYS™ 2010 and cobra e411 and cobra e601. The test has a sensitivity of 3 pg/ml with respect to PlGF. sFlt-1 amounts between 10 to 85,000 pg/ml.

Urea was measured by an in vitro test for the quantitative determination of urea/urea nitrogen in human serum, plasma and urine on Roche/Hitachi cobas c systems. The test can be carried out automatically using different analysers including COBAS® c 311 and COBAS® c 501/502. The assay is a kinetic assay with urease and glutamate dehydrogenase. Urea is hydrolyzed by urease to form ammonium and carbonate. In the second reaction 2-oxoglutarate reacts with ammonium in the presence of glutamate dehydrogenase (GLDH) and the coenzyme NADH to produce L-glutamate. In this reaction 2 moles of NADH are oxidized to $NAD^+$ for each mole of urea hydrolyzed. The rate of decrease in the NADH concentration is directly proportional to the urea concentration in the specimen and is measured photometrically.

Transferrin was measured by using a COBAS INTEGRA® system (ROCHE) for the quantitative immunological determination of human transferrin in serum and plasma. The applied assay is an immunoturbidimetric assay. Human transferrin forms a precipitate with a specific antiserum which is determined turbidimetrically at 340 nm.

SHBG was measured by an electrochemiluminescence immunoassay (ECLIA). The test can be carried out automatically using different analysers including ELECSYS™ 2010 and cobra e411 and cobra e601. In a first incubation step, the sample is contacted with a monoclonal SHBG-specific antibody labeled with a ruthenium complex, thereby forming a sandwich complex. In a second incubation step, streptavidin-coated microparticles are added. The formed complex becomes bound to the solid phase via interaction of biotin and streptavidin. Results are determined via a calibration curve which is instrument specifically generated by 2-point calibration and a master curve provided via the reagent barcode.

Uric acid is determined was determined by applying an enzymatic colorimetric method. In this enzymatic reaction, the peroxide reacts in the presence of peroxidase (POD), N-ethyl-N-(2-hydroxy-3-sulfopropyl)-3-methylaniline (TOOS), and 4-aminophenazone to form a quinone-diimine dye. The intensity of the red color formed is proportional to the uric acid concentration and is determined photometrically.

Ferritin was measured in plasma samples by using the Roche/Hitachi COBAS® C system. The applied assay is a particle enhanced immunoturbidimetric assay. Human ferritin agglutinates with latex particles coated with anti-ferritin antibodies. The precipitate is determined turbidimetrically at 570/800 nm.

Example 3: Results

The analysis described in above led to the following statin therapy response predictions.

Osteopontin (OPN) levels below (but not above) median tend to predict the therapy response to statins in HF patients without CAD (but not in patients with CAD)

sST2 levels below median predict the therapy response to statins in HF patients in patients without CAD ($p=0.04$)

GDF-15 levels above the median predict the therapy response to statins in HF patients without CAD; conversely, GDF-15 levels below the median predict the therapy response to statins in HF patients with CAD (both $p=0.04$)

Urea levels above (but not below) the median predict the therapy response to statins in HF patients with CAD ($p=0.02$) and with a trend also in patients without CAD ($p=0.10$)

Uric acid levels below (but not above) median predict the therapy response to statins in HF patients with CAD ($p=0.03$), but less so in patients without CAD ($p=0.09$)

Transferrin levels above (but not below) the median tend to predict the therapy response to statins in HF patients with CAD ($p=0.06$)

cTnT levels above the median predict the therapy response to statins in HF patients with CAD ($p=0.03$); conversely, cTnT levels below the median tend to predict the therapy response to statins in HF patients without CAD ($p=0.07$)

SHBG levels below the median predict the therapy response to statins in HF patients without CAD ($p=0.04$); conversely, SHBG levels above the median predict the therapy response to statins in HF patients with CAD ($p=0.002$)

sFLt-1 levels below (but not above) median predict the therapy response to statins in HF patients with CAD ($p=0.03$), and less so in patients without CAD ($p=0.10$)

Prealbumin levels above median predict the therapy response to statins in HF patients without CAD ($p=0.04$), and Prealbumin levels below the median tend to predict the therapy response to statins in HF patients with CAD ($p=0.06$)

PLGF levels above median tend to predict the therapy response to statins in HF patients with CAD ($p=0.004$), and less so in patients without CAD ($p=0.08$)

IL-6 levels above median tend to predict the therapy response to statins in HF patients with CAD ($p=0.06$), and less so in patients without CAD ($p=0.15$)

Ferritin levels below median predict the therapy response to statins in HF patients with CAD ($p=0.02$), but not in patients without CAD ($p=0.21$)

hsCRP levels below median predict the therapy response to statins in HF patients with CAD ($p=0.03$); conversely, hsCRP levels above the median tend to predict the therapy response to statins in HF patients without CAD ($p=0.12$)

Not suitable for statin therapy decisions were Cystatin C, S100, P1NP, and Testosteron.

Example 4: Validation

Additionally, the survival analysis was performed for specific drugs of the statin class, i.e. atorvastatin and pravastatin (n=84 and 91, respectively, see FIG. 1). The overall survival analyses in patients with Coronary Artery Disease indicates that the treatment effect of these two statins was not different ($p=0.74$). Accordingly, the data show the effects observed across all statins can also be observed if the patient cohorts are divided according to the type of statin used.

Finally, the analysis was performed for patients being on statin before and during the study vs patients receiving a statin during the course of the study (n=193 vs 95, respectively; see FIG. 1). This analyses indicates that the treatment effect of statins was not different in these two groups (p=0.39) supporting the notion that patients on statins can be grouped for the biomarker specific analysis (disregarding whether they received the statin before or during the study). Accordingly, the data show the effects observed the entire patient cohort can also be observed for patients which were previously treated with a statin and patients which were not treated with a statin (at baseline).

Example 5

A 90 year old male patient with class C heart failure is receiving low doses of enalapril (5 mg/d) and metoprolol (25 mg/d). The patient shows signs of heart failure with elevated NT-proBNP levels (1235 pg/mL). The patient has hypertension (blood pressure 130/85 mm Hg under antihypertensive therapy) and peripheral artery occlusive disease, but does not have Coronary Artery Disease. The treating physician is in doubt as to whether a statin should be added. GDF-15 is determined in a plasma sample obtained from the patient. The GDF-15 value is above 3800 pg/mL. Statin therapy is started (atorvastatin 10 mg/d). The patient remains stable with a good outcome for the next 16 months (no death or hospitalization).

A 79 year old female patient with NYHA class III heart failure is receiving a therapy consisting of aspirin (300 mg/d), clopidogrel (50 mg/d), hydrochlorothiazide (12.5 mg/d), valsartan (80 mg/d) atenololol (100 mg/d), as well as simvastatin 80 mg/d. The patient has had a myocardial infarction at the age of 75 years and was recently hospitalized for an episode of heart failure decompensation. The simvastatin therapy was stopped in the hospital due muscle pain. The treating physician is not sure whether to re-introduce a statin therapy since the patient has had muscle pain that may be due to myopathy. PlGF is determined in a plasma sample obtained from the patient. The PlGF value is above 22 pg/mL. The physician prescribes atorvastatin 20 mg/d and closely monitors creatine kinase to exclude myopathy. The patient remains stable with a good outcome for the next 1.5 years (no death, no hospitalization).

CONCLUSIONS

The use of statin therapy in chronic heart failure (CHF) is not supported by major guidelines. However, it was shown in the context of the present invention that some subgroups of patients suffering from heart failure may benefit from a therapy comprising a statin, whereas some subgroups may not benefit from said therapy. The subgroups can be identified by measuring the level of at least one biomarker selected from GDF-15, Urea, SHBG Uric acid, PLGF IL-6 Transferrin, a cardiac Troponin, sFlt-1 Prealbumin, Ferritin, Osteopontin, sST2 and hsCRP in a sample from a patient. In particular, biomarker levels in blood may predict whether a heart failure patient will derive a benefit or will derive harm from statin therapy. This is advantageous, since the method of the present invention allows to identify those patients which should be treated with a statin and those patients which should not be treated with a statin. Thereby, unnecessary health care costs as well as adverse side effects can be avoided.

The invention claimed is:

1. A method of treating a human patient having heart failure comprising:
   (a) combining a serum or plasma sample from a patient with an antibody or antibodies capable of detection and specific for a biomarker wherein the biomarker is one or more of the following: SHBG (Sex Hormone-Binding Globulin), PLGF (Placental Growth Factor), and/or IL-6 (Interleukin-6);
   (b) detecting the antibody/biomarker complex to determine a level of the at least one biomarker selected from SHBG (Sex Hormone-Binding Globulin), PLGF (Placental Growth Factor), IL-6 (Interleukin-6), in the sample;
   (c) comparing the level of the at least one marker to a respective reference level;
   (d) identifying the patient as more likely to respond to a therapy comprising a statin when the level of the at least one biomarker is indicative for a therapy comprising a statin; and
   (e) administering a statin to the identified patient.

2. The method according to claim 1, wherein the subject has heart failure classified as stage B, C or D according to the ACC/AHA classification, and/or wherein the subject has heart failure classified as NYHA class II, III or IV according to the NYHA classification.

3. The method according to claim 1, wherein the patient also has coronary artery disease.

4. The method of claim 1, wherein
   i) the at least one biomarker is SHBG, and
      a) wherein the patient does not suffer from coronary artery disease, and wherein a level of the biomarker in the sample from the patient below the reference level indicates that the patient is more likely to respond to the therapy comprising a statin, and/or wherein a level of the biomarker in the sample from the patient above the reference level indicates that the patient is less likely to respond to the therapy comprising a statin, or
      b) wherein the patient suffers from coronary artery disease, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin and/or
   ii) the at least one biomarker is PlGF, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin, and/or
   the at least one biomarker is IL-6, and wherein a level of the biomarker in the sample from the patient above the reference level indicates that the patient is more likely to respond to the therapy comprising a statin, and/or wherein a level of the biomarker in the sample from the patient below the reference level indicates that the patient is less likely to respond to the therapy comprising a statin.

5. The method of claim 1 further comprising a step wherein therapy with a statin is initiated or continued if the patient has been identified as likely to respond to a therapy comprising a statin.

6. The method of claim 1, wherein the biomarker measured is SHBG (Sex Hormone-Binding Globulin).

7. The method of claim 1, wherein the biomarker measured is PLGF (Placental Growth Factor).

8. The method of claim 1, wherein the biomarker measured is IL-6 (Interleukin-6).

9. The method according to claim 1, wherein the subject has heart failure classified as stage B or C according to the ACC/AHA classification, and/or wherein the subject has heart failure classified as NYHA class II or III according to the NYHA classification.

10. The method according to claim 1, wherein the patient also has coronary artery disease and wherein the at least one biomarker is PlGF.

* * * * *